(12) United States Patent
Paxson

US009183347B1

(10) Patent No.: US 9,183,347 B1
(45) Date of Patent: Nov. 10, 2015

(54) METHODS AND SYSTEM FOR SIMULATION OF CHEMICAL AND BIOLOGICAL PROCESSES IN A DISTRIBUTED TECHNICAL COMPUTING ENVIRONMENT

(75) Inventor: Ricardo E. Paxson, Boston, MA (US)

(73) Assignee: The MathWorks, Inc., Natick, MA (US)

(*) Notice: Subject to any disclaimer, the term of this patent is extended or adjusted under 35 U.S.C. 154(b) by 1290 days.

(21) Appl. No.: 11/060,995

(22) Filed: Feb. 17, 2005

(51) Int. Cl.
*G06G 7/48* (2006.01)
*G06F 19/12* (2011.01)
*G01N 33/46* (2006.01)

(52) U.S. Cl.
CPC ........................................ *G06F 19/12* (2013.01)

(58) Field of Classification Search
CPC ........................................................ G06F 19/12
See application file for complete search history.

(56) References Cited

U.S. PATENT DOCUMENTS 5,490,097 A * 2/1996 Swenson et al. ................. 703/2
5,761,507 A * 6/1998 Govett .......................... 718/101
8,726,278 B1 5/2014 Shawver et al.

OTHER PUBLICATIONS

Mendes "Biochemistry by numbers:simulation of a biochemical pathway with Gepasi 3" TIBS (1997) vol. 22, pp. 361-363.*
Berkenpas, Monica, "Current products available to perform distributed and/or parallel computing with MATLAB," (2003).
Husbands, Parry Jones Reginald, "Interactive Supercomputing," pp. 1-96 (1999).
Gibson, Michael A. et al., "Efficient Exact Stochastic Simulation of Chemical Systems with Many Species and Many Channels," J. Phys. Chem. A., vol. 104:1876-1889 (2000).
Gillespie, Daniel T. et al., "Exact Stochastic Simulation of Coupled Chemical Reactions," The Journal of Physical Chemistry, vol. 81 (25):2340-2361 (1977).
Panyam, Jayanth et al., "Biodegradable nanoparticles for drug and gene delivery to cells and tissue," Advanced Drug Delivery Reviews, vol. 55:329-347 (2003).
"Parallel Matlab survey" retrieved from the internet at: http://supertech.lcs.mit.edu/-cly/survey.html, 8 pages, Oct. 12, 2003.
"Mathtools.net>MATLAB>Parallel" retrieved from internet at: http://www.mathtools.net/, 2 pages, Oct. 15, 2004 (Print Date).
"gridMathematica, Technical Computing for the Grid," retrieved from the internet at: www.wolfram.com/gridmathematica, 2 pages, 2003.
"Plapack: Parallel Linear Algebra Package," retrieved from the internet at: http://www.cs.utexas.edu/users/plapack/, 2 pages, Nov. 2, 2004 (Print Date).
"Matlab Parallelization toolkit," retrieved from the internet at: http://hem.passagen.se/einar_heiberg/index/html?k, 2 pages, last updated on Nov. 19, 2003.
"DistributePP," retrieved from the internet at: http://www.mathworks.com/matlabcentral/fileexchange/loadFile.do/ojectId=1287&objectType=file, 3 pages, Nov. 2, 2004 (Print Date).
"Netsolve/GridSolve-2.0," retrieved from the internet at: http//icl.ce.utk.edu/netsolve/, 2 pages, Nov. 2, 2004 (Print Date).
"The DP-Toolbox Home Page," retrieved from the internet at: http://www-at.technik.unirostock.de/ra_ac/dp/, 1 page, Jun. 19, 2001.
"Software Documentation:Cornell Multitask Toolbox for MATLAB," retrieved from the internet at: www.tc.cornell.edu/Services/Software/CMTM/overview.html, 5 pages, Nov. 2, 2004 (Print Date).
"PMI" retrieved from the internet at: http://www.mathworks.com/matlabcentral/fileexchange/loadFile.do?objectID=219, last updated on Mar. 12, 2004.
"MATLAB Parallelization Toolkit 1.20," retrieved from the internet at: http://www.mathworks.com/matlabcentral/fileexchange/loadfile.do?objectId=1227, 3 pages, last updated on Nov. 19, 2003.
"MultiMATLAB: MATLAB on Multiple Processors," retrieved from the internet at: http://www.cs.cornell.edu/Info/Peoole/Int/multimatlab.html, 15 pages, May 1996 (Print Date).
"MATmarks: Shared Memory Programming with Matlab," retrieved from the internet at: http://polaris.cs.uiue.edu/matmarks/matmarks.html , 2 pages, 1999.
"Parallel Programming with MatlabMPI," retrieved from the internet at: http://arxiv.org/abs/astro-ph/0107406, 1 page, Jul. 20, 2001.
Parallel Matlab: The Next Generation, J. Kepner and N. Travinin, 7th High Performance Embedded Computing workshop (HPEC 2003), MIT Lincoln Laboratory, Lexington, MA, retrieved from the internet at:http://www.astro.princeton.edu/~ivkepner/, 2 pages, Sep. 23-25, 2003.
"Commsim and Multi Toolbox for MATLAB 5," retrieved from the internet at:http://www.lapsi.eletro.ufrgs.br/Disciplinas/ENG_ELECTRICA/CADENG/Matlab/CommSim/COMMSIM%20for%20MATLAB%205.htm, 2 pages, Sep. 22, 2005 (Print Date).
"Matlab Parallelization Toolkit," retrieved from the interne at: http://www.imy.liu.se/klinfys/einar/misc.html, 4 pages, last updated on Feb. 28, 2005.
"paralize," retrieved from the internet at:http://www.mathworks.com/matlabcentral/files/211/content/paralize/paralize.html, 5 pages, Sep. 22, 2005 (Print Date).
P. L. Springer, "Matpar: parallel extensions for MATLAB", *Proc. Int. Conf. Parallel and Distributed Processing Techniques and Applications*, vol. 3, retrieved from the internet at: http://www-hpc.jpI.nasa.gov/PS/MAPAR/, pp. 1191-1195, 1998.
"Falcon," retrieved from the internet at: http://www.csrd.uiuc.edu/falcon.html, 2 pages, last updated on Feb. 2, 1996.
"AccelChip-MATLAB DSP Algorithmic Synthesis for FPGAs and ASICs," retrieved from the internet at:http://www/acce;chip.com/, 4 pages, Sep. 22, 2005 (Print Date).

(Continued)

*Primary Examiner* — Eric S Dejong
(74) *Attorney, Agent, or Firm* — Harrity & Harrity, LLP

(57) ABSTRACT

Methods and systems are provided for simulating chemical and biological processes in a distributed technical computing environment. A technical computing client may associate a job, comprising one or more tasks, with a chemical or biological process. The technical computing client can distribute these tasks to technical computing workers for execution of the task. The technical computing workers execute the task and may provide a result of the task for the technical computing client. As such, the present invention allows the use of multiple computing resources on a network to perform simulation to facilitate decreasing the computation time.

21 Claims, 22 Drawing Sheets

(56) References Cited

OTHER PUBLICATIONS

"Menhir," retrieved from the internet at: http://www.irisa.fr/caps/PROJECTS/Menhir/menhir/orap/, 2 pages, Feb. 16, 1998.

"Accelerating Matlab," retrieved from the internet at: http://research.microsoft.com/-minka/software/matlab.html, 2 pages, Sep. 22, 2005 (Print Date).

"parmatlab," retrieved from the internet at: http://www.mathworks.com/matlabcentral/fileexchange/loadFile.do?objectId=217&objectType=FILE, 4 pages, last updated on Nov. 19, 2001.

"CONcurrent LABoratory," retrieved from the interne at: http://www.cs.umu.se/research/conlab/, 3 pages, last updated on Dec. 4, 2004.

"Distributed Matlab toolbox," retrieved from the internet at: http://www.geocities.com/kyawtuns/tools/html?200522, 1 pages Sep. 22, 2005 (Print Date).

"SG1-Cray Origin2000 Supercomputer Repository," retrieved from the interne at: http://scv.bu.edu/SVC/Origin2000/matlab/MATLABexample.shtml, 2 pages, last updated on Dec. 12, 2001.

"Parallel Programming with MatlabMPI," retrieved from the internet at: http://www.11.mit.edu/MatlabMPI/, 13 pages, Jul. 20, 2001 (Print Date).

"Matlab Mesh Partitioning and Graph Separator Toolbox," retrieved from the internet at: http://www.cerfacs.fr/algor/Softs/MESHPART/, 3 pages, Feb. 8, 2002.

"MPI Toolbox for Matlab (MPITB)," retrieved from the internet at: http://etcpc7.uqr/mpitb.plip, 2 pages, Sep. 22, 2005 (Print Date).

"RTExpress," retrieved from the interne at: http://www.rtexpress.com/, 2 pages, Sep. 22, 2005 (Print Date).

"Parallel Programming with MPI," retrieved from the internet at: http://www.cs.usfca.edu/mpi/, 2 pages, last updated on Oct. 16, 2002.

"PVM Toolbox for Matlab (PVMTB}," retrieved from the internet at: http://atc.ugr.es/javier-bin/pvmtb_eng, 5 pages, last updated on Apr. 18, 2004.

"qsubfunc," retrieved from the internet at: http://www.sccn.ucsd.edu/·arno/qsubfunc.php, 2 pages, Sep. 22, 2005 (Print Date).

"TMath 0.2: A Tcl Interface to MATLAB and Mathematica," retrieved from the internet at: http://ptolemy.eecs.berkeley.edu/other/tmath0.2/README.html, 9 pages, Jul. 8, 1997.

\* cited by examiner

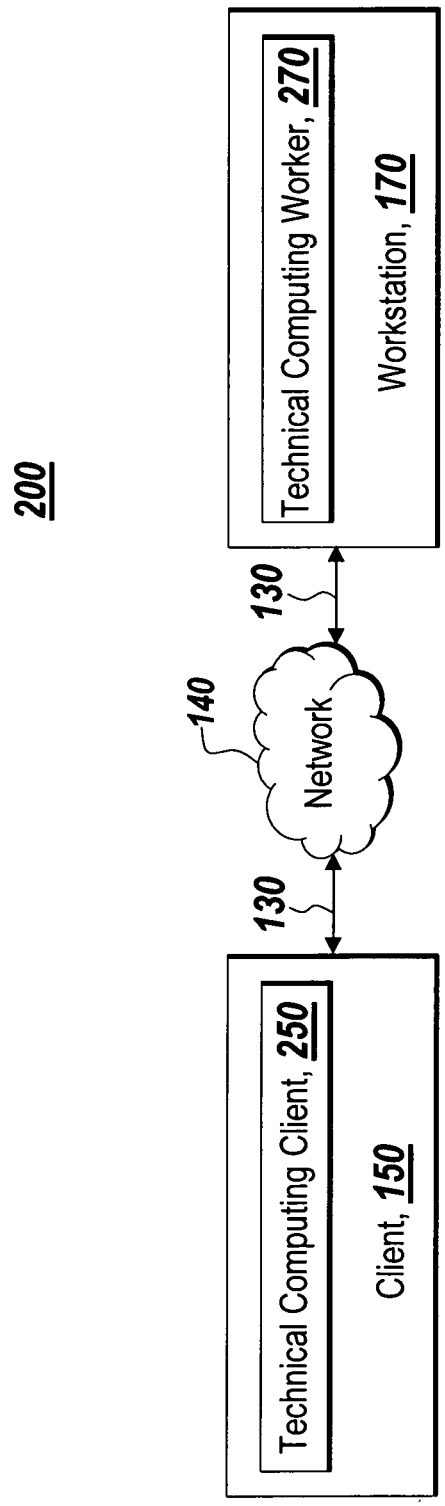

Fig. 6B

Parallel (Distributed + Streaming)

METHODS AND SYSTEM FOR SIMULATION OF CHEMICAL AND BIOLOGICAL PROCESSES IN A DISTRIBUTED TECHNICAL COMPUTING ENVIRONMENT

TECHNICAL FIELD

The present invention generally relates to simulation of chemical and biological processes, and particularly the distribution of the processing of simulations of chemical and biological processes.

BACKGROUND INFORMATION

The development of new drug targets by the pharmaceutical industry is time-consuming and expensive because a large number of possible targets need to be tested before the molecule or compound with the desired properties is found or formulated. Along the same argument, but not for the purpose of new drug development, are the activities or synthetic biology. Here, biological entities are designed to perform a particular function. A particular example of this case is the development of biological nanomachines that might for example be used as programmed drug delivery systems. (See J. Panyam, V. Labhasetwar, Biodegradable nanoparticles for drug and gene delivery to cells and tissue, Advanced Drug Delivery Reviews, 55 (2003) 329-347.) As in drug discovery efforts, the formulation of a compound with desired properties is difficult due to the large variety of possible targets and the even larger context or system in which they must perform their function. Currently much of the work done to investigate the properties of these compounds is done in a wet-lab requiring many tedious and error prone experiments.

Development of chemical substances and nanomachinery, in addition to being time-consuming, can generate potentially dangerous intermediate substances. For example, a molecule used as transport for a drug in a drug delivery system could by its mere presence in the organism, stimulate the overproduction of some other protein. The overexpressed protein could act as a lethal toxin for the organism. Another possible complication is that the nanomachinery itself may mutate over time and either lose its original function or worse adversely interfere with the viability of the organism.

Another problem facing the drug development activity is that, due to the cumbersome nature of experimental data collection, it is typical to limit experiments by narrowing the range of tested inputs and in general isolating the subsystem of interest. This limitation allows for the possibility that new drugs have unforeseen side-effects.

Moreover, current methods of obtaining data for biological processes are even more time-consuming than those associated with chemical processes, because the latter generally require laboratory experiments that lead to animal experiments and clinical trials. From these trials and experiments, data are obtained which, again, usually focus on a very narrow part of the biological system. Only after numerous costly trial-and-error clinical trials and constant redesigning of the clinical use of the drug to account for lessons learned from the most recent clinical trial, is a drug having adequate safety and efficacy finally realized. This process of clinical trial design and redesign, multiple clinical trials and, in some situations, multiple drug redesigns requires great expense of time and money. Even then, the effort may not produce a marketable drug. While conclusions may be drawn by assimilating experimental data and published information, it is difficult, if not impossible, to synthesize the relationships among all the available data and knowledge.

The various challenges faced by the aforementioned activities in chemical and biochemical research make it desirable to have software and methods for modeling, simulating, and analyzing biological processes in-silico rather than in-vitro or in-vivo. The goal of this approach is to provide a more comprehensive view of these biological systems prior to costly experiments and to clinical trials thereby reducing the search space for drug targets and useful nanoparticles.

The simulation of biological systems requires the use of many modes of computation such as continuous time, discrete step, hybrid, particle level among others. The need for these arises from the various simplifying assumptions made in order to make the problem tractable using today's computer technology and resources. At the most basic level, the particle based approach, every molecule in a cell is accounted for individually. Given the number of molecular components in a cell this approach is prohibitively expensive unless it is used for a relatively small number of molecules in the overall system. Approximations can be made which result in a significant reduction in the computational cost. One class of simplifications group like-molecules and treat the entire group as one variable. This approach allows the development of probabilistic methods and well as differential ones, which are much less expensive in terms of computational cost. In effect, there is a continuum of methods varying from high fidelity, compute intensive to approximate and less expensive methods. Hybrid solvers are those that mix one or more of these methods to optimize the use of computational resources while achieving a high level of fidelity.

One such method which accounts for the random nature of molecular interactions is called a stochastic simulator; it may be used to simulate the time varying behavior of a collection of chemically interacting molecules in a chemical or biological system. In this case, the simulator maintains a list of reactions in the chemical or biological system that "could" happen and moves the state of the system forward through time in a two-step process. First, the simulator determines which reaction in the list of reactions will be the next to occur, and the time at which that reaction will occur. Second, the simulator simulates the reaction, adjusting the quantities of each type of molecule as specified by the stoichiometry of the reaction. This process is repeated iteratively as the system is marched forward in time. ($^{see}$ D. Gillespie, J. Phys. Chemistry, 81, 25 (1977).)

However, a single workstation can be limiting to the size of the problem that can be solved, because of the relationship of the computing power of the workstation to the computing power necessary to execute computing intensive iterative processing of complex problems in a reasonable time. For example, a simulation of a large complex biological model may take a reasonable time to run with a single computation with a specified set of parameters. However, the analysis of the problem may also require the model be computed multiple times with a different set of parameters to understand the behavior of the model under varied conditions. This could require thousands of computations to analyze the problem as desired, and the single computer would take a substantial amount of time to perform these simulations. In this case, the single computer would be allocated full-time to performing the computation while many computer resources on the network may be idle. Additionally, the benefit of the interactive features of the software is reduced as the computation time increases.

With many biological and chemical systems requiring larger and more complex modeling, computations accordingly become more resource intensive and time-consuming. When a computation becomes so large and complex that it cannot be completed in a reasonable amount of time on a single computer, a solution to decrease the computation time is needed.

However, a single workstation can be limiting to the size of the problem that can be solved, because of the relationship of the computing power of the workstation to the computing power necessary to execute computing intensive iterative processing of complex problems in a reasonable time. For example, a simulation of a large complex biological model may take a reasonable time to run with a single computation with a specified set of parameters. However, the analysis of the problem may also require the model be computed multiple times with a different set of parameters to understand the behavior of the model under varied conditions. This could require thousands of computations to analyze the problem as desired, and the single computer would take a substantial amount of time to perform these simulations. In this case, the single computer would be allocated full-time to performing the computation while many computer resources on the network may be idle. Additionally, the benefit of the interactive features of the software is reduced as the computation time increases.

With many biological and chemical systems requiring larger and more complex modeling, computations accordingly become more resource intensive and time-consuming. When a computation becomes so large and complex that it cannot be completed in a reasonable amount of time on a single computer, a solution to decrease the computation time is needed.

SUMMARY OF THE INVENTION

The present invention provides methods and a system for simulating chemical and biological processes in a distributed technical computing environment. A technical computing client may associate a job, comprising one or more tasks, with a chemical or biological process. The technical computing client can distribute these tasks to technical computing workers for execution of the task. The technical computing workers execute the task and may provide a result of the task for the technical computing client. As such, the present invention allows the use of multiple computing resources on a network to perform simulation to facilitate decreasing the computation time.

In accordance with a first aspect, the invention involves a method for simulating chemical reactions in a distributed technical computing environment. The method comprises the steps of associating, on a technical computing client, a first task with a simulation of a chemical reaction; and submitting the first task to an automatic task distribution mechanism to make the first task available to a technical computing worker. The automatic task distribution mechanism may then provide the first task to a first technical computing worker. The first technical computing worker has a technical computing environment for executing the first task. The result of the executed task may then be provided back to the automatic task distribution mechanism and technical computing client.

In accordance with another aspect, a method is provided for simulating a chemical reaction in an object-oriented distributed technical computing environment. The method comprises the steps of associating, on a technical computing client, a first task object with a simulation of a chemical reaction; and submitting, by the technical computing client, the first task object for distribution to a technical computing worker.

In accordance with another aspect, the invention involves a system for simulating chemical reactions in a distributed technical computing environment. The system comprises a technical computing client associating a first task with a simulation of a chemical reaction and submitting the first task to distribute for processing in a technical computing environment; and an automatic task distribution mechanism in communication with the technical computing client, the automatic task distribution mechanism receiving the first task submitted by the technical computing client and making the first task available to a technical computing worker. The system may also include a first technical computing worker in communication with the automatic task distribution mechanism, the technical computing worker having a technical computing environment for performing technical computing of a task, the first technical computing worker obtaining the first task from the automatic task distribution mechanism.

In accordance with another aspect, the invention involves a medium holding instructions executable in an electronic device. The instructions comprise associating, on a technical computing client, a first task with a simulation of a chemical reaction; and submitting the first task to an automatic task distribution mechanism to make the first task available to a technical computing worker. The instructions may also include providing, by the automatic task distribution mechanism, the first task to a first technical computing worker to execute the first task, the first technical computing worker having a technical computing environment.

In accordance with another aspect, the invention involves a method for distributing the processing of a simulation of a chemical reaction in a technical computing environment. The method comprises the steps of associating, on a technical computing client, a first job with a simulation of a chemical reaction, the first job object associated with one or more tasks, a first task of the one or more tasks associated with a simulation of a chemical reaction; providing to a first job manager, the first job object; and providing, by the first job manager, the first task to an automatic task distribution mechanism to make the first task available to a technical computing worker for execution. The technical worker may then execute the first task and provide the result back to the automatic task distribution mechanism, job manager, and technical computing client.

In accordance with another aspect, a method is provided for simulating a chemical reaction in an object-oriented distributed technical computing environment. The method comprises the steps of associating, on a technical computing client, a first job object with a simulation of a chemical reaction, the first job object associated with one or more tasks objects, a first task of the one or more tasks associated with a simulation of a chemical reaction; providing to a first job manager, the first job object; and providing, by the first job manager, the first task object to an automatic task distribution mechanism to make the first task object available to a technical computing worker for execution.

In accordance with another aspect, the invention involves a method for simulating a biological process comprising a plurality of chemical reactions in a distributed technical computing environment. The method comprises (a) associating, on a technical computing client, a first job with a simulation of a biological process, the first job comprising one or more tasks associated with the chemical reactions of the biological process being simulated; and (b) providing to a first job manager, the first job object; and (c) providing, by the first job manager, the first task first job to an automatic task distribution mechanism to make the first task available to a technical computing worker for execution. The first task may then be provided to the first technical worker. The first technical computing worker has a technical computing environment for executing the first task. The result of the executed task may then be provided back to the automatic task distribution mechanism and technical computing client.

The details of various embodiments of the invention are set forth in the accompanying drawings and the description below. Other features and advantages of the invention will become apparent from the description, the drawings and the claims.

BRIEF DESCRIPTION OF THE DRAWINGS

The foregoing and other objects, aspects, features, and advantages of the invention will become more apparent and may be better understood by referring to the following description taken in conjunction with the accompanying drawings, in which:

FIG. 2A is a block diagram of the components of an embodiment of the present invention in a two-node networked computer system;

FIG. 6B is another screenshot depicting an embodiment of a tabular modeling environment;

DETAILED DESCRIPTION

Figure 1A:
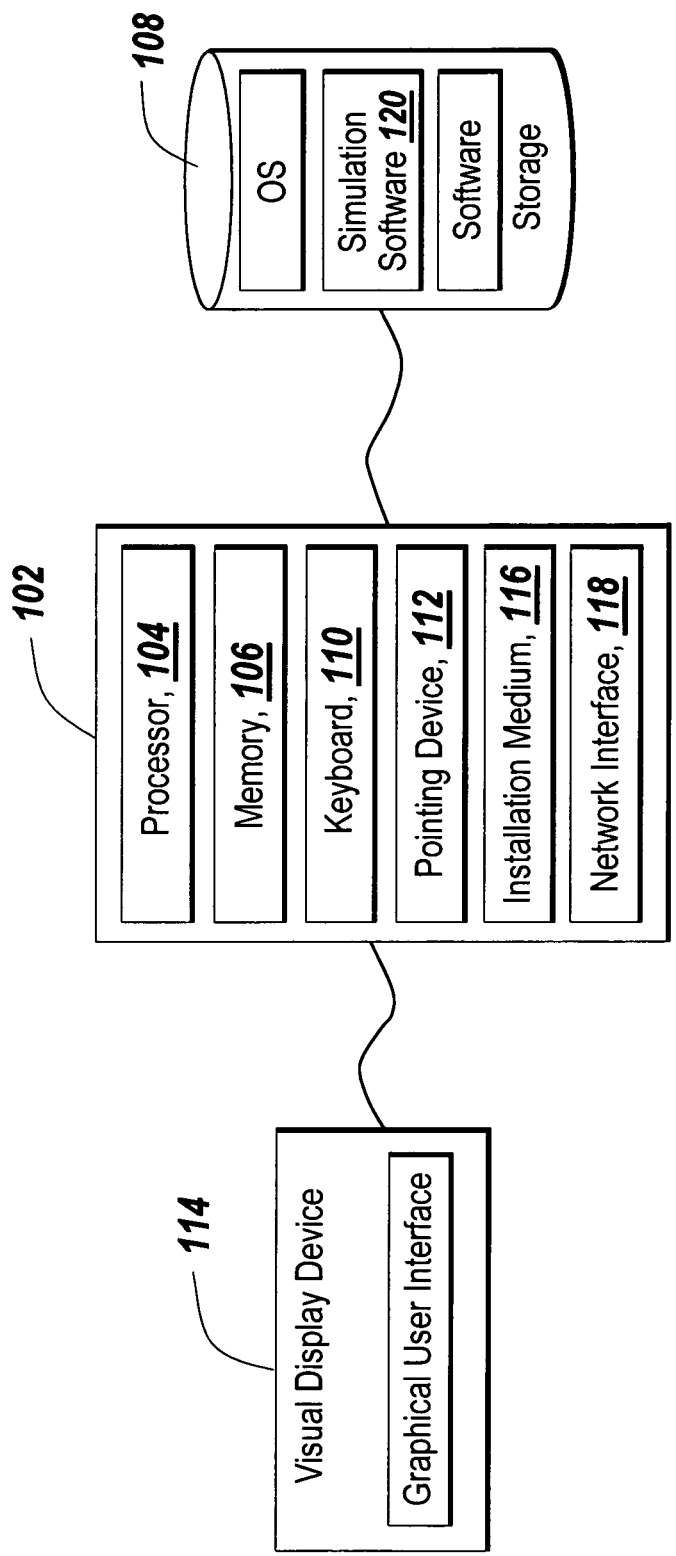
FIG. 1A is a block diagram of a computing device for practicing an embodiment of the present invention.

Certain embodiments of the present invention are described below. It is, however, expressly noted that the present invention is not limited to these embodiments, but rather the intention is that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The illustrative embodiment of the present invention provides for dynamic distribution of simulations of chemical and biological processes by associating tasks with the chemical or biological processes. The tasks are distributed from a technical computing client to remote technical computing workers for execution of the tasks on multiple computers systems. Tasks associated with the simulation of chemical and biological reactions on a technical computing client and may be additionally organized into jobs. A job is a logical unit of activities, or tasks that are processed and/or managed collectively. A task defines a technical computing command, such as a MATLAB® command, to be executed, and the number of arguments and any input data to the arguments. A job is a group of one or more tasks. The task can be directly distributed by the technical computing client to one or more technical computing workers. A technical computing worker executes a task and may return a result to the technical computing client.

Additionally, a task or a group of tasks, in a job, can be submitted to an automatic task distribution mechanism to distribute the one or more tasks automatically to one or more technical computing workers providing technical computing services. The technical computing client does not need to specify or have knowledge of the technical computing workers in order for the task to be distributed to and computed by a technical computing worker. The automatic task distribution mechanism can distribute tasks to technical computing workers that are anonymous to any technical computing clients. The technical computing workers perform the task and may return as a result the output data generated from the execution of the task. The result may be returned to the automatic task distribution mechanism, which, in turn, may provide the result to the technical computing client.

Furthermore, the illustrative embodiment provides for an object-oriented interface in a technical computing environment to dynamically distribute tasks or jobs directly or indirectly, via the automatic task distribution mechanism, to one or more technical computing workers. The object oriented interface provides a programming interface for a technical computing client to distribute tasks for execution by technical computing workers.

Dynamic systems, such as biological processes and chemical reactions, are typically modeled as sets of differential, difference, algebraic, and/or recursive equations. At any given instant of time, these equations may be viewed as relationships between the system's output response ("outputs"), the system's input stimuli ("inputs") at that time, the current state of the system, the system parameters, and time.

The state of the system may be thought of as a numerical representation of the dynamically changing configuration of the system. For instance, in a physical system modeling a simple pendulum, the state may be viewed as the current position and velocity of the pendulum. Similarly, a signal-processing system that filters a signal would maintain a set of previous inputs as the state. The system parameters are the numerical representation of the static (unchanging) configuration of the system and may be viewed as constant coefficients in the system's equations. For the pendulum example, a parameter is the length of pendulum and for the filter example; a parameter is the values of the filter taps.

Types of mathematical models used in the study of dynamic systems include differential equations, difference equations, algebraic equations, and hybrid models. For modeling biological processes and chemical reactions, a stochastic model may be useful. This model describes systems using stochastic techniques, such as Gillespie, Gibson/Bruck, and τ-leaping.

For example, the Gillespie stochastic technique uses an algorithm to numerically simulate the time evolution of a given chemical system. In the Gillespie technique, reaction events given selected probabilities of occurring, and the events which occur change the probabilities of subsequent events. The algorithm determines, for a system in a given state, the next reaction to occur and the time that the next reaction occurs using probability. The algorithm is based on a quantity P(t,u), which is the probability that a reaction u will occur at the time interval t. The probabilities are based on the classical rate coefficients (k), the volume of the container, which can be a cell, a partition of a cell, a compartment of the cell, such as the nucleus or other organelles, or other container, and the concentration of reactants in a given reaction. Once a time and reaction have been computed, the method carries out the reaction, i.e., it updates the state of the system to reflect the transformation of reactants into products, then increments the time by t and determines another reaction to occur and when the reaction will occur. The Gillespie technique is described in detail in the article: Gillespie, D. T. 1977, *Exact Stochastic Simulation of Coupled Chemical Reactions*, Journal of Physical Chemistry, vol. 81, pp. 2340-2361.

The Gibson/Bruck stochastic technique is a variation of the Gillespie algorithm and described in the journal article Gibson, M. A., and J. Bruck, *Efficient Exact Stochastic Simulation of Chemical Systems with Many Species and Many Channels*, 2000 Journal of Physical Chemistry A, vol. 104, pp. 1876-1889.

One skilled in the art will recognize that any suitable stochastic technique for simulating the time evolution of a given chemical system may be utilized in the present invention. When simulated stochastically, this reaction occurs at a random time determined according to a probability distribution associated with that reaction. The reaction time may be determined by drawing a random number from the probability distribution.

FIG. 1A depicts an environment suitable for practicing an illustrative embodiment of the present invention. The environment includes a computing device 102 having memory 106, on which software according to one embodiment of the present invention may be stored, a processor (CPU) 104 for executing software stored in the memory 106, and other programs for controlling system hardware. The memory 106 may comprise a computer system memory or random access memory such as DRAM, SRAM, EDO RAM, etc. The memory 106 may comprise other types of memory as well, or combinations thereof. A human user may interact with the computing device 102 through a visual display device 114 such as a computer monitor, which may include a graphical user interface (GUI). The computing device 102 may include other I/O devices such a keyboard 110 and a pointing device 112, for example a mouse, for receiving input from a user. Optionally, the keyboard 110 and the pointing device 112 may be connected to the visual display device 114. The computing device 102 may include other suitable conventional I/O peripherals. The computing device 102 may support any suitable installation medium 116, a CD-ROM, floppy disks, tape device, USB device, hard-drive or any other device suitable for installing software programs such as software handling the distribution of chemical and biological process simulations of the present invention (hereinafter referred to as simulation distribution software 120). The computing device 102 may further comprise a storage device 108, such as a hard-drive or CD-ROM, for storing an operating system and other related software, and for storing application software programs such as simulation distribution software 120 of the present invention.

Additionally, the computing device 102 may include a network interface 118 to interface to a Local Area Network (LAN), Wide Area Network (WAN) or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. The network interface 118 may comprise a built-in network adapter, network interface card, PCMCIA network card, card bus network adapter, wireless network adapter, USB network adapter, modem or any other device suitable for interfacing the computing device 118 to any type of network capable of communication and performing the operations described herein. Moreover, the computing device 102 may be any computer system such as a workstation, desktop computer, server, laptop, handheld computer or other form of computing or telecommunications device that is capable of communication and that has sufficient processor power and memory capacity to perform the operations described herein.

Figure 1B:
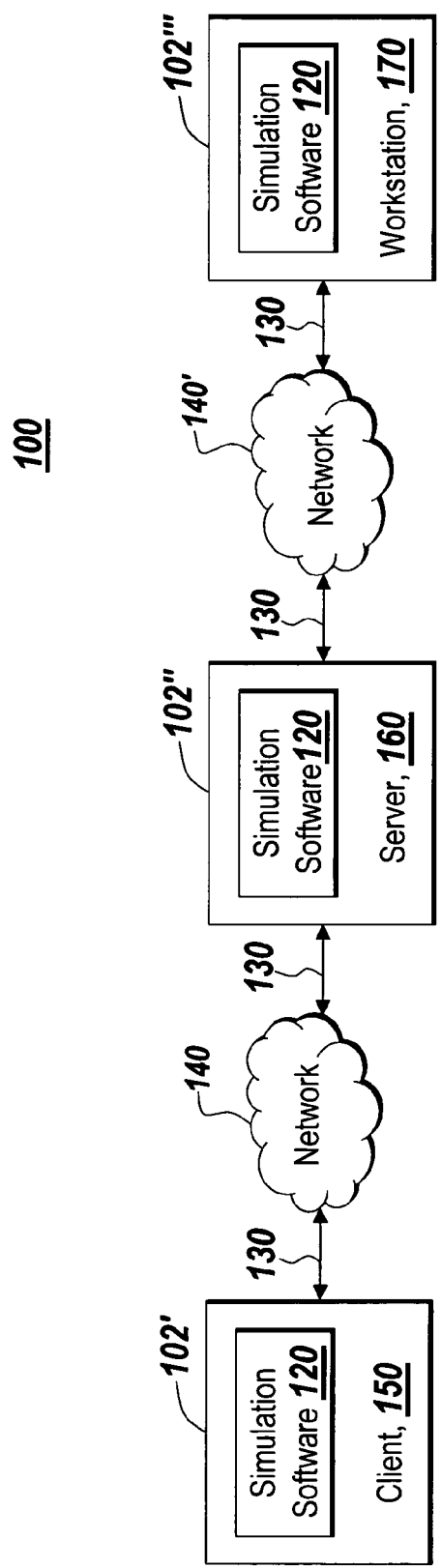
FIG. 1B is a block diagram of a distributed computing system for practicing an illustrative embodiment of the present invention.

FIG. 1A depicts simulation distribution software 120 of the present invention running in a stand-alone system configuration of a single computing device 102. FIG. 1B depicts another environment suitable for practicing an illustrative embodiment of the present invention, where functionality is distributed across multiple computing devices (102', 102" and 102'"). In a broad overview, the system 100 depicts a multiple-tier or n-tier networked computer system for performing distributed software applications such as the distributed technical computing environment of the present invention. The system 100 includes a client 150 (e.g., a first computing device 102') in communications through a network communication channel 130 with a server computer 160, also known as a server, (e.g., a second computing device 102") over a network 140 and the server in communications through a network communications channel 130 with a workstation (e.g., a third computing device 102'") over the network 140'. The client 150, the server 160, and the workstation 170 can be connected 130 to the networks 140 and/or 140' through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. Each of the client 150, server 160 and workstation 170 can be any type of computing device (102', 102" and 102'") as described above and respectively configured to be capable of computing and communicating the operations described herein.

In one embodiment, each of the client 150, server 160 and workstation 170 are configured to and capable of providing at least a portion simulation distribution of the present invention. As a distributed system, there are one or more software components that run on each of the client 150, server 160 and workstation 170, respectively, and work in communication and in collaboration with each other to meet the functionality of the overall application. For example, the client 150 may hold a graphical modeling environment that is capable of specifying block diagram models and technical computing tasks to analyze the model. The client 150 may have software components configured to and capable of submitting the tasks to the server 160. The server 160 may have software components configured to and capable of receiving the tasks submitted by the client 150 and for determining a workstation 170 to assign the task for technical computing. The workstation 170 may hold software components capable of providing a technical computing environment to perform technical computing of the tasks assigned from the server 160 and submitted by the client 150. In summary, the technical computing environment and software components may be deployed across one or more different computing devices in various network topologies and configurations.

FIG. 2A depicts an illustrative embodiment of a system of the present invention. In brief overview, the system 200 in this embodiment is a two-node distributed system comprising a technical computing client application 250, or technical computing client, running on a client 150 computer and a technical computing worker application 270, or technical computing worker, running on a workstation 170. The technical computing client 250 is in communications with the technical computing worker 170 through a network communications channel 130 over a network 140.

The technical computing client 250 can be a technical computing software application that provides a technical computing and graphical modeling environment for generating block diagram models and to define mathematical algorithms for simulating models of biological and chemical processes. The technical computing client 250 may include all or a portion of the functionality provided by the standalone desktop application of MATLAB®. One ordinarily skilled in the art will appreciate the various combinations of client types that may access the functionality of the system.

With an application programming interface and/or programming language of the technical computing client 250, functions can be defined representing a biological or chemical process to be executed by either a technical computing environment local to the client computer 150, or remote on the workstation 270. The local technical computing environment may be part of the technical computing client 250, or a technical computing worker running on the client computer 150. The programming language includes mechanisms, described below in more detail, to define a task to be distributed to a technical computing environment and to communicate the task to the technical computing worker 270 on the workstation 170, or alternatively, on the client 150.

The distributed functionality features of the client 250 allows the technical computing client 250 to use the computing resources that may be available from a technical computing worker 270 on the workstation 170 to perform simulation of a biological or chemical reaction. This frees up the technical computing client 250 to perform other tasks, or the client computer 150 to execute other software applications.

The technical computing worker 270 of the system 200 can be a technical computing software application that provides a technical computing environment for performing technical computing of tasks, such as those tasks defined or created by the technical computing client 250. The technical computing worker 270 can be an application, module, service, software component, or a session, which includes support for technical computing of functions defined in the programming language of MATLAB®. A session is an instance of a running technical computing worker 270 by which a technical computing client can connect and access its functionality. The technical computing worker 270 can include all the functionality and software components of the technical computing client 250, or it can just include those software components it may need to perform technical computing of tasks it receives for execution. The technical computing worker 270 may be configured to and capable of running any of the modules, libraries or software components of the MATLAB® product family. As such, the technical computing worker 270 may have all or a portion of the software components of MATLAB® installed on the workstation 170, or alternatively, accessible on another system in the network 140. The technical computing worker 270 has mechanisms, described in detail later, to receive a task distributed from the technical computing client 250. The technical computing worker 270 is capable of performing the task as if the technical computing client 250 was performing the task in its own technical computing environment. The technical computing worker 270 also has mechanisms, to return a result generated by the execution of the task to the technical computing client 250.

The technical computing worker 270 can be available on an as needed basis to the technical computing client 250. When not performing technical computing of tasks from the technical computing client 250, the workstation 170 of the technical computing worker 270 can be executing other software programs, or the technical computing worker 270 can perform execution of tasks from other technical computing clients.

Figure 2B:
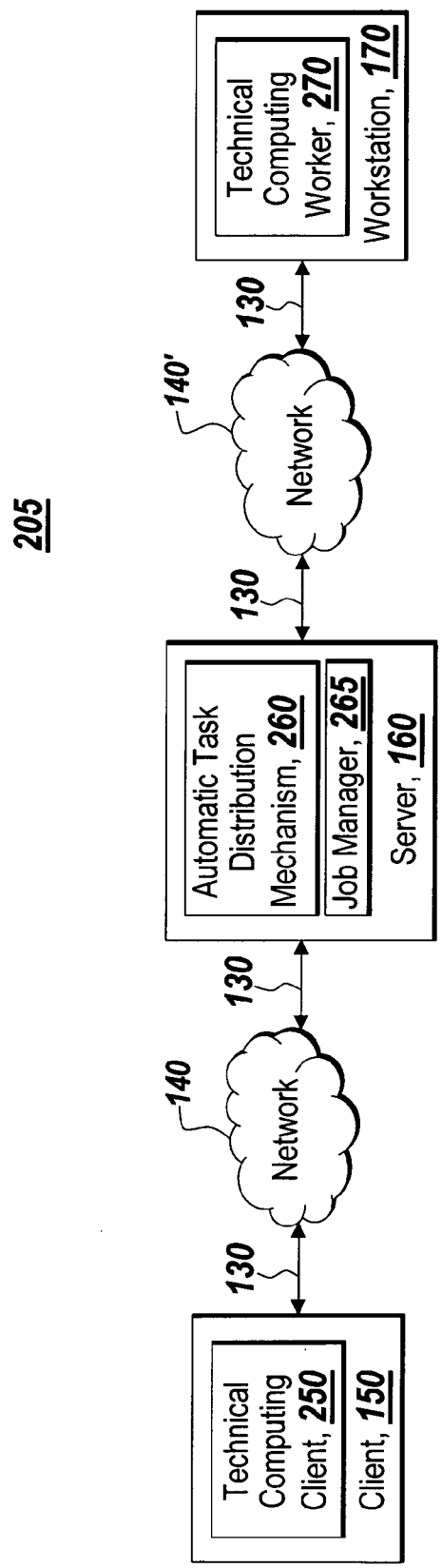
FIG. 2B is a block diagram of the components of an alternative embodiment of the present invention in a multi-tier networked computer system.

FIG. 2B shows another illustrative embodiment of the system of the present invention in a multi-tier distributed computer system as depicted in FIG. 2B. The multi-tier distributed system 205 includes a technical computing client 250 running on a client computer 150 in communications over a network communication channel 130 to a server 160 on a network 140. The server 160 comprises an automatic task distribution mechanism 260 and a job manager 265. The job manager 265 interfaces with the automatic task distribution mechanism 260 on the server 160. The automatic task distribution mechanism 260 communicates over a network communication channel 130 on the network 140 to the technical computing worker 270 on the workstation 170.

The automatic task distribution mechanism 260 comprises one or more application software components to provide for the automatic distribution of tasks from the technical computing client 250 to the technical computing worker 270. The automatic task distribution mechanism 260 allows the technical computing client 250 to delegate the management of task distribution to the automatic task distribution mechanism 260. For example, a task can be defined and submitted to the automatic task distribution mechanism 260 without specifying which technical computing worker 270 is to perform the technical computing of the task. The technical computing client 250 does not need to know the specifics of the technical computing worker 270. The technical computing client can define a function to submit the task to the automatic task distribution mechanism 260, and get a result of the task from the automatic task distribution mechanism 260. As such, the automatic task distribution mechanism provides a level of indirection between the technical computing client 250 and the technical computing worker 270.

This eases the distributed programming and integration burden on the technical computing client 250. The technical computing client 250 does not need to have prior knowledge of the availability of the technical computing worker 270. For multiple task submissions from the technical computing client 250, the automatic task distribution mechanism 260 can manage and handle the delegations of the tasks to the same technical computing worker 270, or to other technical computing workers, e.g., 270 and 270', and hold the results of the tasks on behalf of the technical computing client 250 for retrieval after the completion of technical computing of all the distributed tasks.

As part of the system, a job manager module 265, or "job manager", is included as an interface to the task and result management functionality of the automatic task distribution mechanism 260. The job manager 265 can comprise an object-oriented interface to provide control of delegating tasks and obtaining results in the multi-tiered distributed system 205. The job manager 265 provides a level of programming and integration abstraction above the details of inter-process communications and workflow between the automatic task distribution mechanism 260 and the technical computing worker 270. The job manager 265 also provides an interface for managing a group of tasks collectively as a single unit called a job, and on behalf of a technical computing client 250, submitting those tasks making up the job, and obtaining the results of each of the tasks until the job is completed. Alternatively, the automatic task distribution mechanism 260 can include the functionality and object-oriented interface of the job manager 265, or the automatic task distribution mechanism 260 and the job manager 265 can be combined into a single application, or software component. In an exemplary embodiment, the job manager 265 comprises both the functionality of the job manager 265 and the automatic task distribution mechanism 260. One ordinarily skilled in the art will recognize the functions and operations of the job manager 265 and the automatic task distribution mechanism 260 can be combined in various software components, applications and interfaces.

Figure 2C:
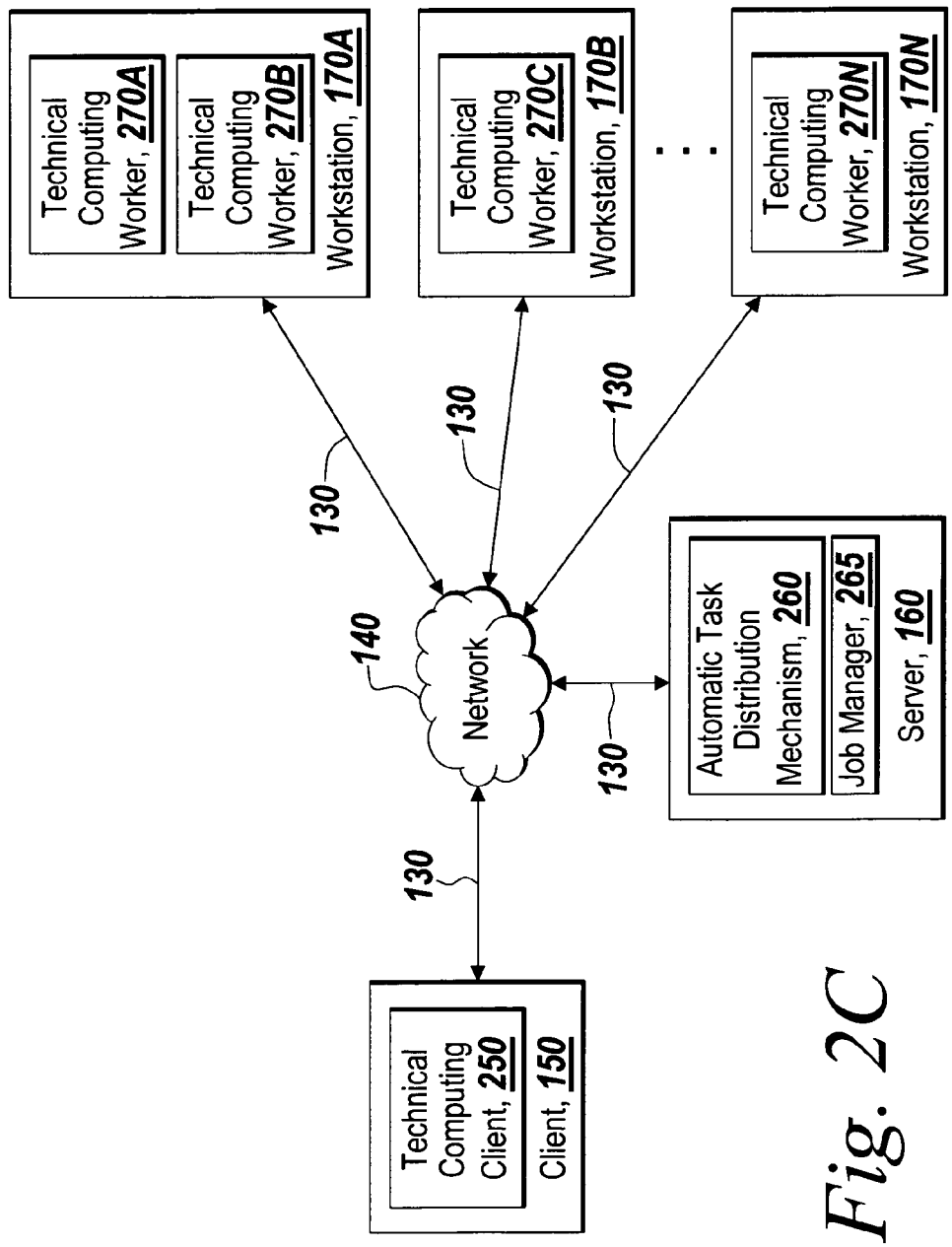
FIG. 2C is a block diagram of the components of an exemplary embodiment of the present invention in a distributed network computer system.

Referring now to FIG. 2C, an exemplary embodiment of the present invention is shown with multiple technical computing workers 270A-270N hosted on a plurality of workstations 170A-170N. The technical computing client 250 may be in communication through the network communication channel 130 on the network 140 with one, some or all of the technical computing workers 270A-270N. In a similar manner, the automatic task distribution mechanism 260 may be in communication through the network communication channel 130 on the network 140 with one, some or all of the technical computing workers 270A-270N. As such, the technical computing client 250 and/or the automatic task distribution mechanism 260 can distribute tasks to multiple technical computing workers 270A-270N to scale the distributed system and increase computation time of tasks. As also shown in FIG. 2C, the technical computing workers 270A-270B can be hosted on the same workstation 170A, or a single technical computing worker 270C can have a dedicated workstation 170B. Alternatively, one or more of the technical computing workers 270A-270N can be hosted on either the client 150 or the server 160.

The computing devices (102, 102', 102", 102''') depicted in FIGS. 1A and 1B can be running any operating system such as any of the versions of the Microsoft® Windows operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. Furthermore, the software components can be capable of and configured to operate on the operating system that may be running on any of the computing device (e.g., 102, 102', 102", 102'''). Additionally, each of the client 150, the server 160 and the workstation 170 can be running the same or different operating systems. One ordinarily skilled in the art will recognize the various combinations of operating systems and processors that can be running on any of the computing devices (102, 102', 102", and 102''').

Although the present invention is discussed above in terms of distributing software components across the computing devices of a client 150, server 160 and workstation 170, any other system and/or deployment architecture that combines and/or distributes one or more of the technical computing client 250, job manager 265, automatic task distribution mechanism 260 and technical computing worker 270 across any other computing devices and operating systems available in the network 140 may be used. Alternatively, all the software components can run on a single computing device 102, such as the client 150, server 160 or the workstation 170.

Figure 3A:
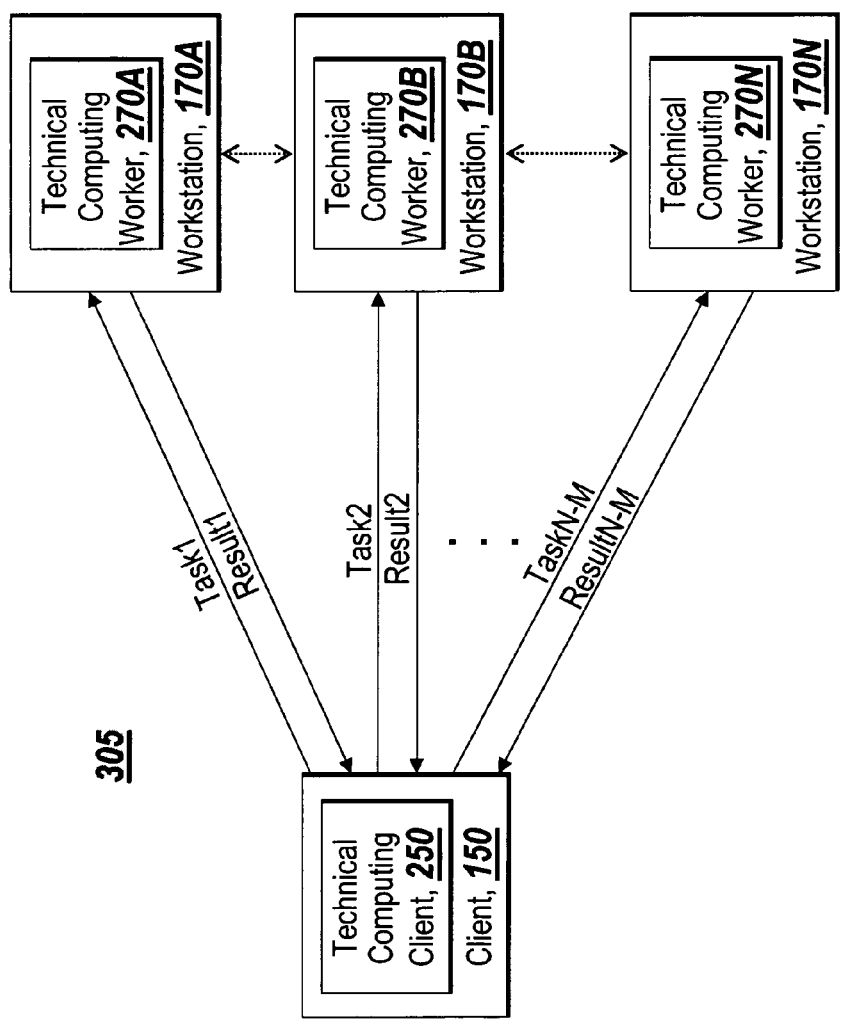
FIG. 3A is a block diagram of the direct distribution mode of operation of the present invention.
Figure 3B:
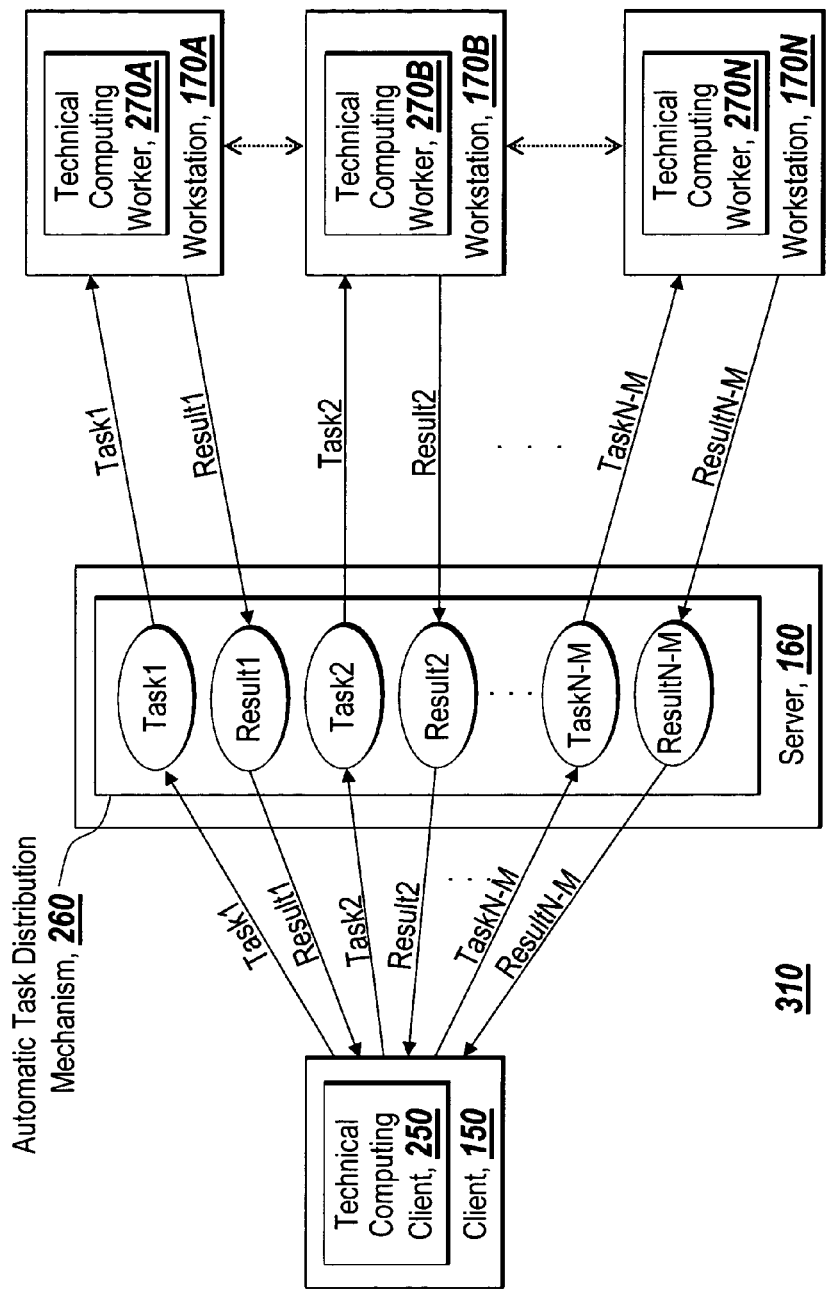
FIG. 3B is a block diagram of the automatic distribution mode of operation of the present invention.
Figure 3C:
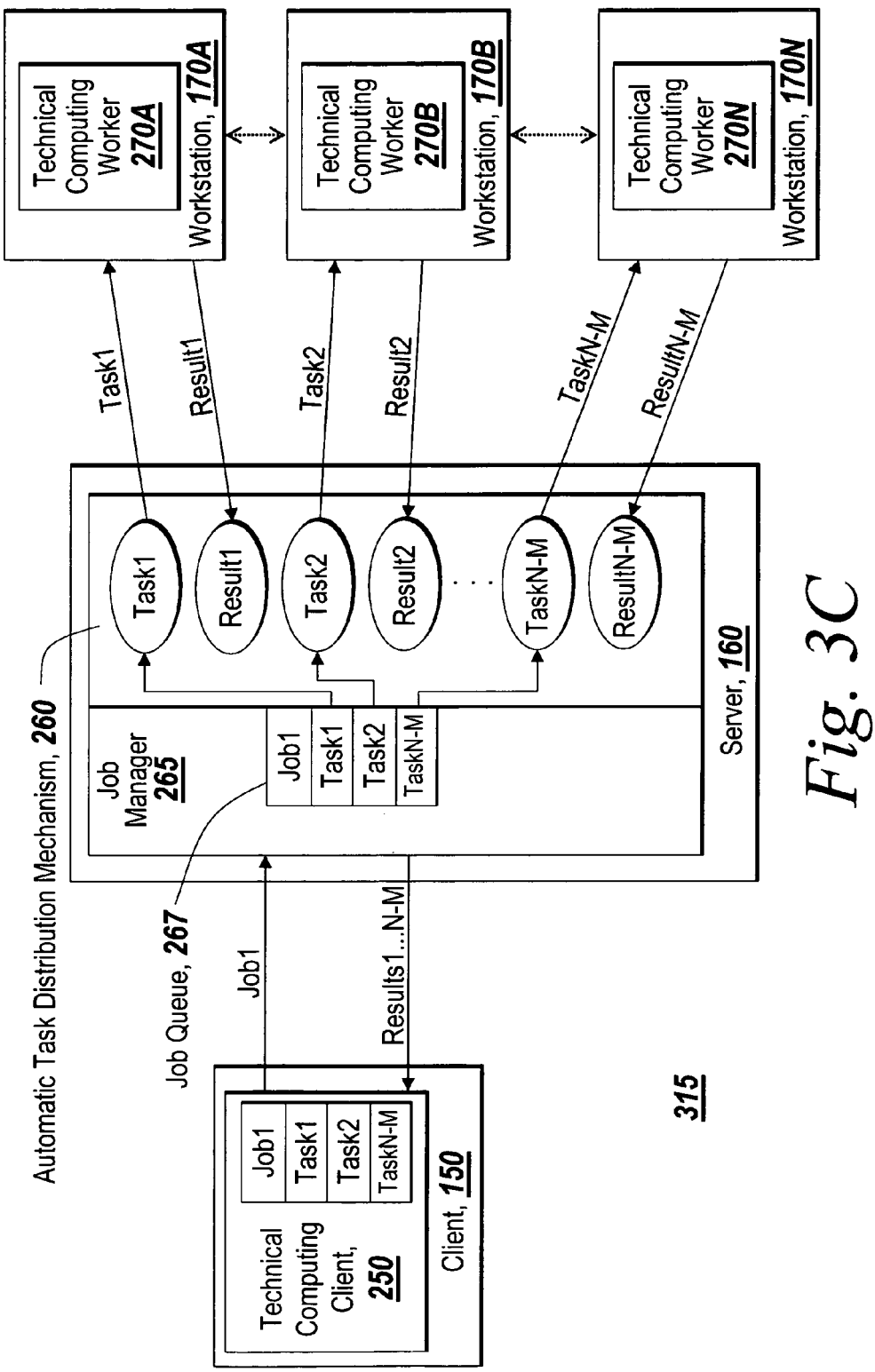
FIG. 3C is a block diagram of the batch automatic distribution mode of operation of the present invention.
Figure 3D:
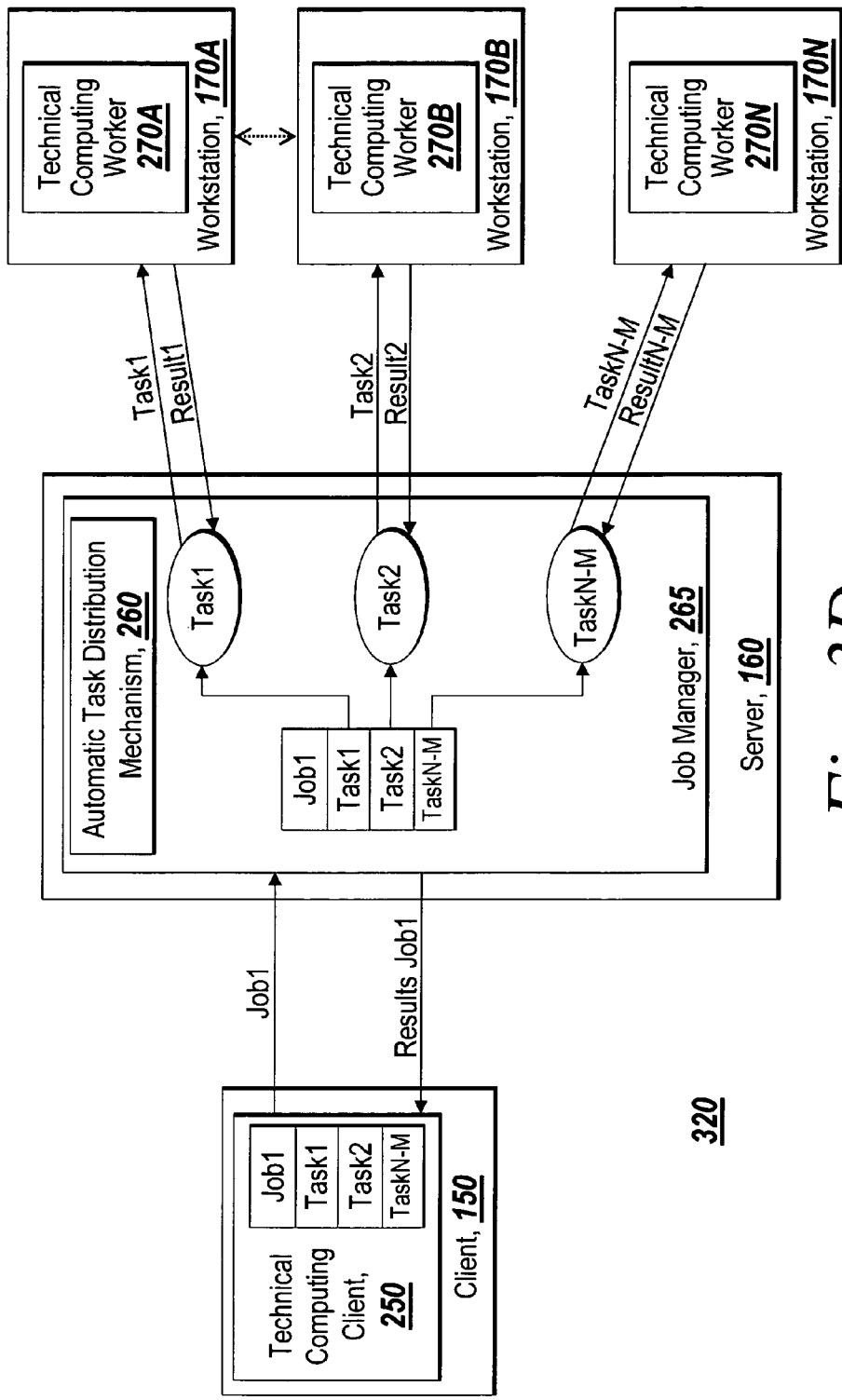
FIG. 3D is a block diagram of an exemplary embodiment of the batch automatic distribution mode of operation of the present invention.

The system of the present invention provides flexibility in methods of task distribution with multiple modes of operation. In FIGS. 3A, 3B and 3C, three modes of task distribution of Simulation distribution software are shown. FIG. 3A depicts a direct distribution mode, FIG. 3B, an automated distribution mode and FIG. 3C, a batch mode of automated distribution. Additionally, FIG. 3D depicts an exemplary embodiment of the batch mode of automated distribution.

The direct distribution system 305 of FIG. 3A is intended for those users who desire a high level of control over which technical computing worker 270A-270N executes a particular task. In brief overview of the direct distribution system 305, the technical computing client 250 is in communications with a plurality of technical computing workers, 270A-270N, each running on their own workstation 170A-170N. In an alternative embodiment, one or more of these technical computing workers 270A-270N can be running on the same computing device, e.g., workstation 270A, or on the client 150 or the server 160. This direct distribution system 305 allows a task to be sent to a particular technical computing worker, e.g., technical computing worker 270A of a plurality of technical computing workers 270A-270N. Then, the technical computing client 250 can continue with other work while the specified technical computing worker, e.g., technical computing worker 270A, is performing technical computing of the submitted task. Some time after submitting the task to the technical computing worker 270A, the technical computing client 250 can then obtain the result of the task from the technical computing worker 270A. Furthermore, each technical computing worker 270N can process multiple tasks, e.g., TaskN-M, and for each task produce a result, e.g., ResultN-M.

Alternatively, the technical computing worker 270A may perform technical computing of a task without returning a result, or may return information acknowledging completion of the task. This mode of task distribution is useful for a computer network with a relatively small number of known workstations 170A-170N and technical computing workers 270A-270N. A task can be delegated to a specified technical computing worker running 270A on a workstation 170A that has a higher speed configuration than the other workstations 170B-170N. For example, a longer task could be executed on such a workstation 170A in order to speed the overall computation time.

As further depicted in FIG. 3A, the technical computing client 250 of the direct distribution system 305 can submit multiple tasks (e.g., TaskN-M) to each of the multiple technical computing workers 270A-270N. For example, the technical computing client 250 submits task 1 to technical computing worker 270A, submits task 2 to technical computing worker 270B, and submits task N to technical computing worker 270N. The technical computing client 250 can submit task1, task2 and taskN-M one immediately after another or within a certain time between each other. As such, the technical computing workers 270A-270N can be performing technical computing of their respective tasks independently and in parallel to each other. Alternatively, the technical computing workers 270A-270N may perform technical computing of their respective task while the other technical computing workers are idle.

In another embodiment, the technical computing workers 270A-270N may include interfaces and communication channels to interact with each other as depicted by the phantom arrowed lines between the technical computing workers 270A-270N in FIG. 3A. In such an embodiment, technical computing worker 270A may perform a portion of technical computing on task1, and then submit task1, and optionally, any generated result or other data, for further technical computing by technical computing worker 270B. Also, the technical computing worker 270A may also submit the result of its technical computing of task1 to the technical computing client 250, before or after, submitting the task to technical computing worker 270B for further processing. Technical computing worker 270B may in turn perform technical computing of task1, and subsequently submit task1 for further processing by technical computing worker 270N. For additional configurability, the technical computing workers 270A-270N can obtain information with the task about the identification of other technical computing workers 270A-270N in the system. This information would be used to communicate and interact with another technical computing worker. Alternatively, a technical computing worker 270A may find another technical computing worker 270B-270N by making a function or system call, or a method call to a service provider on the network 140. In such a configuration, technical computing workers 270A-270N can either execute tasks independently and in parallel to each other, or also execute tasks serially and subsequent to each other.

Referring now to FIG. 3B, the automated task distribution mode embodied in system 310 is intended to provide a configuration where the user does not want to control which technical computing worker 270A-270N executes a particular task. In brief overview of the automated distribution mode of system 310, a technical computing client 250 is in communication with the automatic task distribution mechanism 260 running on the server 160. The automatic task distribution mechanism 260 is in communications with a plurality of technical computing workers 270A-270N. Under this mode of operation, the technical computing client 250 is not required to have any specific knowledge of the technical computing workers 270A-270N, e.g., the name of the workstation running a technical computing worker 270A-270N, or the availability of the technical computing worker 270A-270N to perform technical computing of a task. In alternative embodiments, it may have prior knowledge of all or a portion of the technical computing workers 270A-270N available on the network. Even with knowledge of the name or availability of technical computing workers 270A-270N on the network 140, the technical computing client 250 can choose not to specify the name of a particular technical computing worker to perform the task, and let the automated distribution mechanism distribute the task to any available technical computing worker 270A-270N.

In FIG. 3B, the technical computing client 250 submits one or more tasks (Task1-TaskN-M) to the automatic task distribution mechanism 260. These tasks can be submitted sequentially or in an order and frequency as specified by the technical computing client 250. The automatic task distribution mechanism 260 obtains the tasks (Task1-TaskN-M) to make then available for distribution to any of the technical computing workers 270A-270N. A technical computing worker 270A-270N takes a task from the automatic task distribution mechanism 260 for technical computing of the task, computes a result for the task and provides the result to the automatic task distribution mechanism 260. For example, technical computing worker 270A takes task 1 from the automatic task distribution mechanism 260, computes a result, Result 1, for task 1, and submits Result 1 to the automatic task distribution mechanism 260. The automatic task distribution mechanism 260 makes the results (Result1-ResultN-M) available to the technical computing client 250 as they get submitted from the technical computing worker 270A-270N generating and submitting the respective result. At a time or method determined by the technical computing client 250, the technical computing client 250 obtains the results of the computed tasks from the automatic task distribution mechanism 260. For example, the technical computing client 250 may obtain all the results (Result1-ResultN-M) at the same time after all the results have been computed, or each result may be obtained after it becomes available in the automatic task distribution mechanism 260. Accordingly, the technical computing client 250 can determine the order and frequency of obtaining one or more of the results. As with the direct distribution mode, the technical computing workers 270A-270N can also communicate and interact with each other, as depicted by the phantom arrowed lines between the technical computing workers 270A-270N in FIG. 3B, to execute tasks both serially and in parallel by submitting a task to another technical computing worker 270A-270N.

The batch mode of automated task distribution embodied in system 315 of FIG. 3C is intended to provide a configuration where the user can specify a group of related tasks as a job and provide the batch of tasks, or the job, to the automatic task distribution mechanism 260. In brief overview of the batch mode of the automatic distribution system 315, a technical computing client 250 is in communication with the job manager 265 on the server 160. The job manager 265 interfaces and communicates with the automatic task distribution mechanism 260 running on the same server 160. Each of the technical computing workers 270A-270N is in communication with the automatic task distribution mechanism 260. A job manager 265 interfaces with and is associated with one automatic task distribution mechanism 260. Alternatively, the job manager 265 and the automatic task distribution mechanism could be on different servers, e.g., 160 and 160'. Additionally, a plurality of job managers and automatic task distribution mechanisms could be running on a single server 160 or each on their own server (160', 160", etc). Each of the plurality of job managers interface with and are associated with one of the plurality of automatic distribution mechanisms. This allows the distributed system to scale the number of instances of the job manager 265 and the automatic distribution mechanism 260 to handle additional multiple technical computing clients 250 distributing tasks.

In batch mode as depicted in FIG. 3C, the technical computing client 250 defines the job. The technical computing client 250 has a programming language environment by which it can declare tasks, declare a job and associate the tasks with the job. Instead of submitting each task separately as depicted in FIG. 3B, the technical computing client 250 submits the job containing all the associated tasks to the job manager 265. The job manager 265 is a software component that provides an object-oriented interface to the automatic task distribution mechanism 260. The job manager 265 obtains the tasks from the job and provides the tasks to the automatic task distribution mechanism 260 for technical computing workers 270A-270N to take and compute results. For example, technical computing client 250 associates a job, Job1, with a set of three tasks: Task1, Task2 and TaskN-M, with a chemical process. The technical computing client 250 then submits Job1 to the job manager 265. The job manager 265 obtains Job1 and obtains each of the tasks, Task1-TaskN-M from Job 1. Then, according to the configured logic of the job manager 265, described in more detail below, the job manager 265 submits each of the tasks to the automatic task distribution mechanism 260 for execution by a technical computing worker 270A-270N. Technical computing worker 270A may take Task1 from the automatic task distribution mechanism 260, compute a Result1 for Task1 and provide the Result1 to the automatic task distribution mechanism 260. Technical computing worker 270B and technical computing worker 270N, in a similar fashion, compute and provide results for Task2 and TaskN-M respectively. The job manager 265 then obtains the set of results for the completed job of Job1 and provides the results of each of the tasks to the technical computing client 250.

The job manager 265 further comprises a queue 267 for arranging and handling submitted jobs. For example, the job manager 265 may handle jobs in a first-in first-out (FIFO) manner. In this case, the job manager 265 does not process the next job until all the tasks from the current job have been processed by the automatic task distribution mechanism 260. Additionally, the job manager 265 using the queue 267 supports handling multiple job submissions and task distribution from multiple technical computing clients 250. If a first technical computing client 250 submits a job, Job1, the job manager 265 places that job first in the queue 267. If a second technical computing client, e.g., 250', submits a second Job, for example, Job 2, the job manager places the job in the queue behind the Job1 from the first client. In this manner, all technical computing clients (250, 250', 250") accessing the services of the job manager 265 get serviced for task distribution. One ordinarily skilled in the art will recognize that the job manager 265 could implement a variety of algorithms for processing jobs in a job queue 267 and for handling multiple technical computing clients (250, 250', 250"). For example, a user may be able to specify a priority level for a specified job, or the logic of the job manager 265 may make task distributing and processing decisions based on the configuration and availability of technical computing workers 270A-270B to determine a preferred or optimal selection of technical computing of jobs and tasks.

As with the other distribution modes of FIG. 3A and FIG. 3B, the technical computing workers 270A-270N in batch mode can also communicate and interact with each other as shown by the phantom arrowed lines between technical computing workers 270A-270N in FIG. 3C. This allows the technical computing workers 270A-270N to execute tasks both serially and in parallel by submitting a task to another technical computing worker. As part of the information associated with the task obtained by a technical computing worker or by other means, such as a system or function call, or a method call to a service, a technical computing worker 270A can obtain information about the other technical computing workers 270B-270N assigned to or working on tasks associated with a specific job, or available on the network 140.

The exemplary embodiment of the batch mode of automated task distribution system 320 of FIG. 3D depicts a configuration where the job manager 265 contains the automatic task distribution mechanism 260. In brief overview of system 320, a technical computing client 250 is in communication with the job manager 265 on the server 160. The job manager 265 comprises a task distribution mechanism 260 running as part of the job manager 265 on the same server 160. The job manager 265 further comprises a queue 267 for arranging and handling submitted jobs. The technical computing workers 270A-270N are in communication with the job manager 265 to receive tasks from the automatic task distribution mechanism 260 of the job manager 265.

In batch mode operation as depicted in FIG. 3D, the technical computing client 250 defines the job comprised of related tasks. Instead of submitting each task separately as depicted in FIG. 3B, the technical computing client 250 submits the job containing all the related tasks to the job manager 265. The job manager 265 obtains the tasks from the job and submits the tasks, via an automatic task distribution mechanism 260, to the technical computing workers 270A-270N to perform technical computing. For example, technical computing client 250 associates a job, Job1, having a set of three tasks: Task1, Task2 and TaskN-M; with a chemical reaction. The technical computing client 250 then submits Job1 to the job manager 265. The job manager 265 obtains Job1 and obtains each of the tasks, Task1-TaskN-M, from Job 1. Then, the automatic task distribution mechanism 260 of the job manager 265 submits each of the tasks to a technical computing worker 270A-270N for execution. For example, the job manager 265 may submit Task 1 to technical computing worker 270A to compute and produce a Result1 for Task1. Technical computing worker 270A provides the Result1 to the job manager 265. In a similar fashion, the job manager 265 may submit Task2 and TaskN-M to technical computing worker 270B and technical computing worker 270N with each technical computing worker 270A and 270B providing the results for Task2 and TaskN-M respectively to the job manager 265. When all the results from each of the tasks of Job1 are received, the job manager 265 then provides the results of each of the tasks of Job 1 to the technical computing client 250. The result is then available for display or review by a user on the technical computing client 250.

In the batch mode of operation of depicted in Figured 3C and 3D, the job manager 265 or automatic task distribution mechanism 260 can be configured to define the minimum and maximum numbers of technical computing workers 270A-270N to perform the tasks associated with a job. This feature can be configured on a job by job basis. Alternatively, it may be configured for a portion or all of the jobs. The configuration of these settings can be facilitated through parameters associated with a submitted job, such as in one or more properties of a job object, or in one or more fields of a data structure representing a job. Alternatively, these settings may be facilitated through any interface of the job manager 265 or automatic task distribution mechanism 260, such as in a configuration file, graphical user interface, command or message or any other means by which values for these settings may be set.

The system (e.g. 315 or 320) can compare the number of technical computing workers 270A-270N registered, or otherwise available, with the job manager 265 or automatic task distribution mechanism 260 against the configured setting of the minimum number of technical computing workers parameter. The system may not start a job unless there is a minimum number of technical computing workers 270A-270N registered or available to work on the job. In a similar manner, the system can check the number of available or registered technical computing workers 270A-270N against the setting of the maximum number of technical computing workers parameter. As the system distributes tasks of a job, it can make sure not to distribute tasks to more than the defined number of technical computing workers 270A-270N. In some embodiments, the minimum number of technical computing workers will be set to a value equal to the setting of the maximum number of technical computing workers. In such a case, the system may only start the job if the minimum number of technical computing workers 270A-270A are available or registered to start the job, and may not use any more technical computing workers 270A-270N than the minimum setting. This is useful for cases where the user wants to configure a job to have each task be assigned to and run on separate technical computing workers 270A-270N. For example, a job may have 5 tasks and the minimum and maximum technical computing worker settings may be set to 5.

Additionally, in any of the embodiments depicted in FIGS. 3A-3D, the system can determine or select the technical computer worker 270A-270N to work on a task by operational and/or performance characteristics of the technical computing worker 270A-270N and/or workstation 170A-170N. For example, a technical computing worker 270A may work on a task based on the version of simulation software that is installed on the workstation 170A or that the technical computing worker 270A is capable of running. Additionally, the technical computing worker 270A-270N and workstation 170A-170N may have a specification or profile, such as a benchmark comparison results file, which provides a description of any operational and performance characteristics of the version of software running on that specific computing device 102 of the workstation 170A. This profile can be in comparison to known benchmarks of operational and performance characteristics of Simulation distribution software running on certain computing devices (102, 102"), with specified versions of Simulation distribution software, operating systems and other related software, or any other system component or attribute that may impact the operation or performance of simulation software. This profile may be described in a file accessible over the network or retrievable through an interface mechanism of the technical computing worker 270A-270N. Furthermore, the system may determine the technical computing worker 270A-270N to work on a task by any configuration or properties set on the technical computing worker 270A-270N or workstation 170A-170N. For determining a technical computing worker 270A-270N to work on a task, the system may discover any configuration, properties, and operational and performance characteristics of the simulation software of a technical computing worker 270A-270N running on a workstation 170A-170N through any interface of the technical computing worker 270A-N or workstation 170A-170N, such as, for example, in a file, graphical user interface, command or message.

Figure 4:
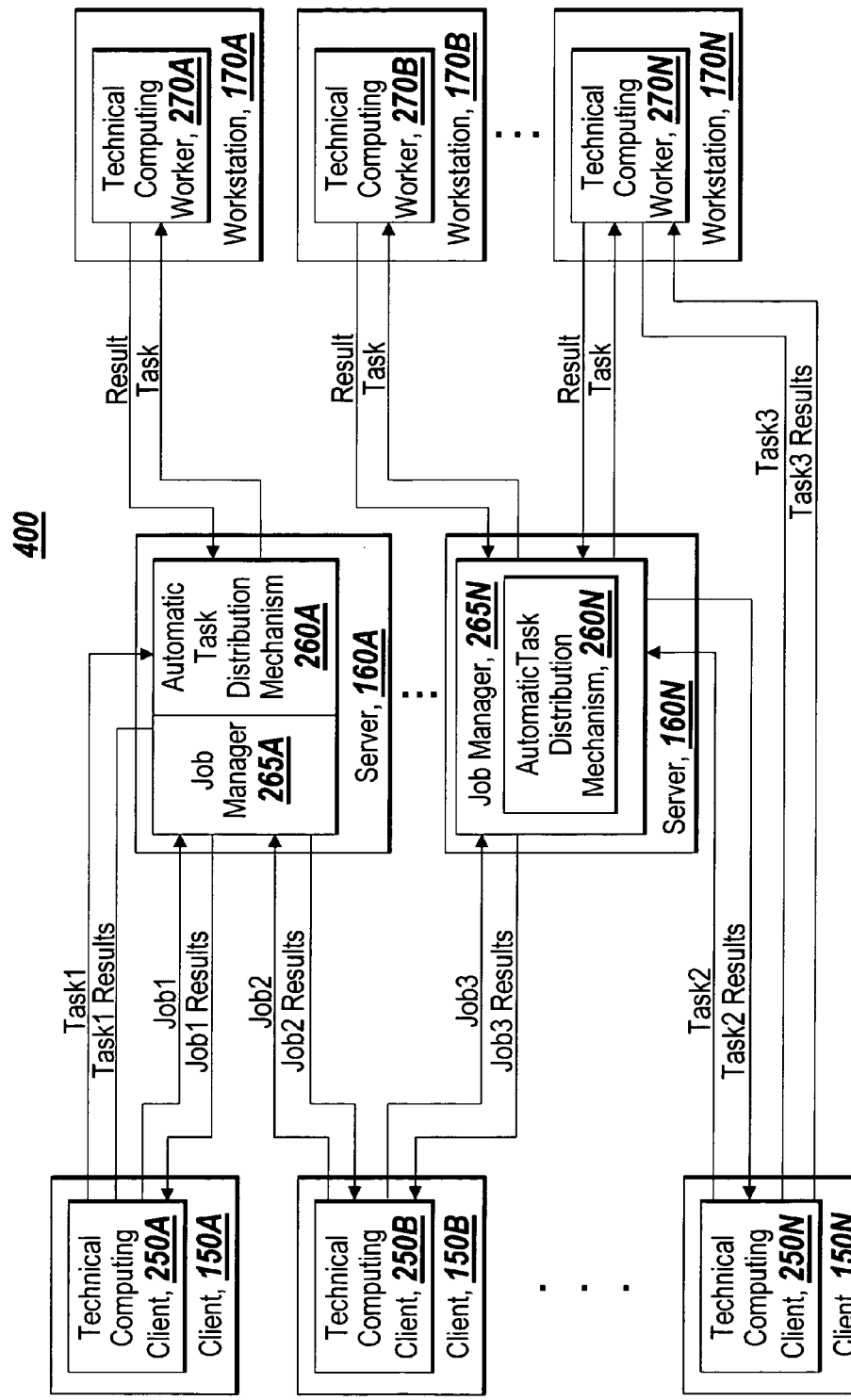
FIG. 4 is a block diagram illustrating a multiple mode of operation embodiment of the present invention.

The present invention also provides additional flexibility in that the multiple modes of task distribution can be performed concurrently in the distributed system. FIG. 4 is an illustrative embodiment of the present invention showing the distributed application performing, concurrently, the combination of the modes of operation depicted in FIGS. 3A-3C. Additionally, the distributed system 400 is depicted supporting multiple clients 250A-250N communicating with multiple job managers 265A-265N and multiple automatic task distribution mechanisms 260A-260N. With these multiple modes of operation, any technical computing client 250A-250N can distribute tasks directly to a technical computing worker 270A-270N, submit tasks to the automatic task distribution mechanism 260, or submit a job to the job manager 265. In the depicted multi-client distributed system 400, a plurality of technical computing clients 250A-250N are in communication with one or more job managers 265A-265N. The job manager 265A can be a separate component interfacing to the automatic task distribution mechanism 260A, or the job manager 265N can be a single application comprising the functionality of the automatic task distribution mechanism 260N. The one or more technical computing workers 270A-270B are in communication with the one or more job managers 265N or the one or more automatic task distribution mechanisms 260A. The distributed architecture of the present invention allows for a scalable and flexible distributed technical computing environment supporting a variety of deployments and network topologies.

For example, as shown in FIG. 4, a technical computing client 250A can operate in both the direct distribution mode and the batch automated distribution mode. As such, technical computing client 250A can submit a task to and receive a result from the automatic task distribution mechanism 260A without using the job manager 265A. In another instance, technical computing client 250A can submit a job, Job1, to the job manager 265A for task distribution by the automatic task distribution mechanism 260A to receive results from the job, such as Job1Results. In another example of FIG. 4, technical computing client 250B can operate in batch automated distribution mode but submit jobs separately to a first job manager 265A running on a first server 160A and a second job manager 265N running on a second server 160N. In yet another example, technical computing client 250N operates in both the automated distribution and direct distribution modes. Technical computing client 250N submits a task, Task2, to automatic task distribution mechanism 260N and receives a result, Task2Result, from computing by a technical computing worker 270A-270N assigned by the system 400. Technical computing client 250N also directly submits a task to technical computing worker 270N and receives a computed result directly from the technical computing worker 270N. One ordinarily skilled in the art will appreciate the various combinations of deployments that can occur with such a distributed system 400 with multiple modes of operation. As such, the present invention offers scalability and flexibility for distributed processing of complex technical computing requirements.

Figure 5A:
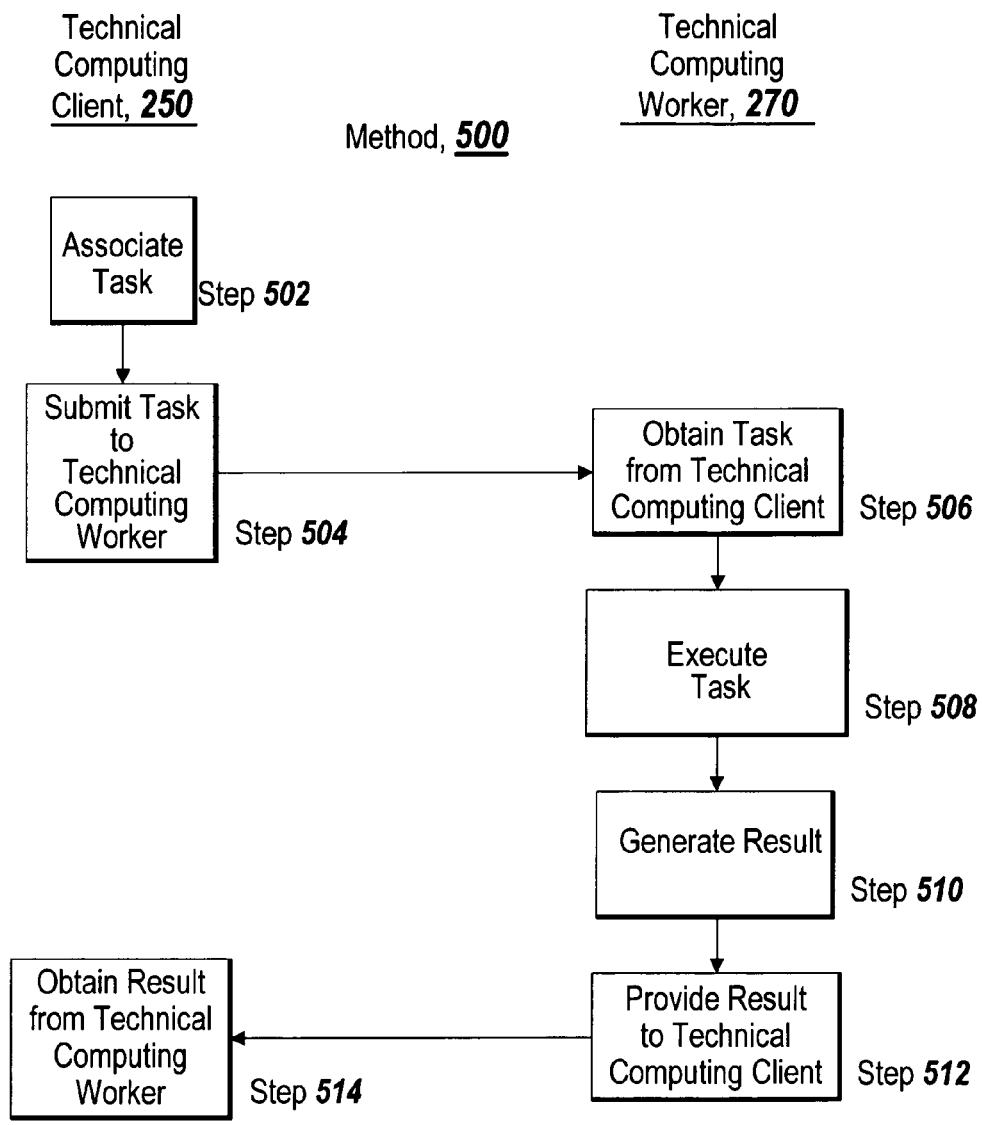
FIG. 5A is a flow diagram of steps performed in an embodiment of FIG. 3A.
Figure 5B:
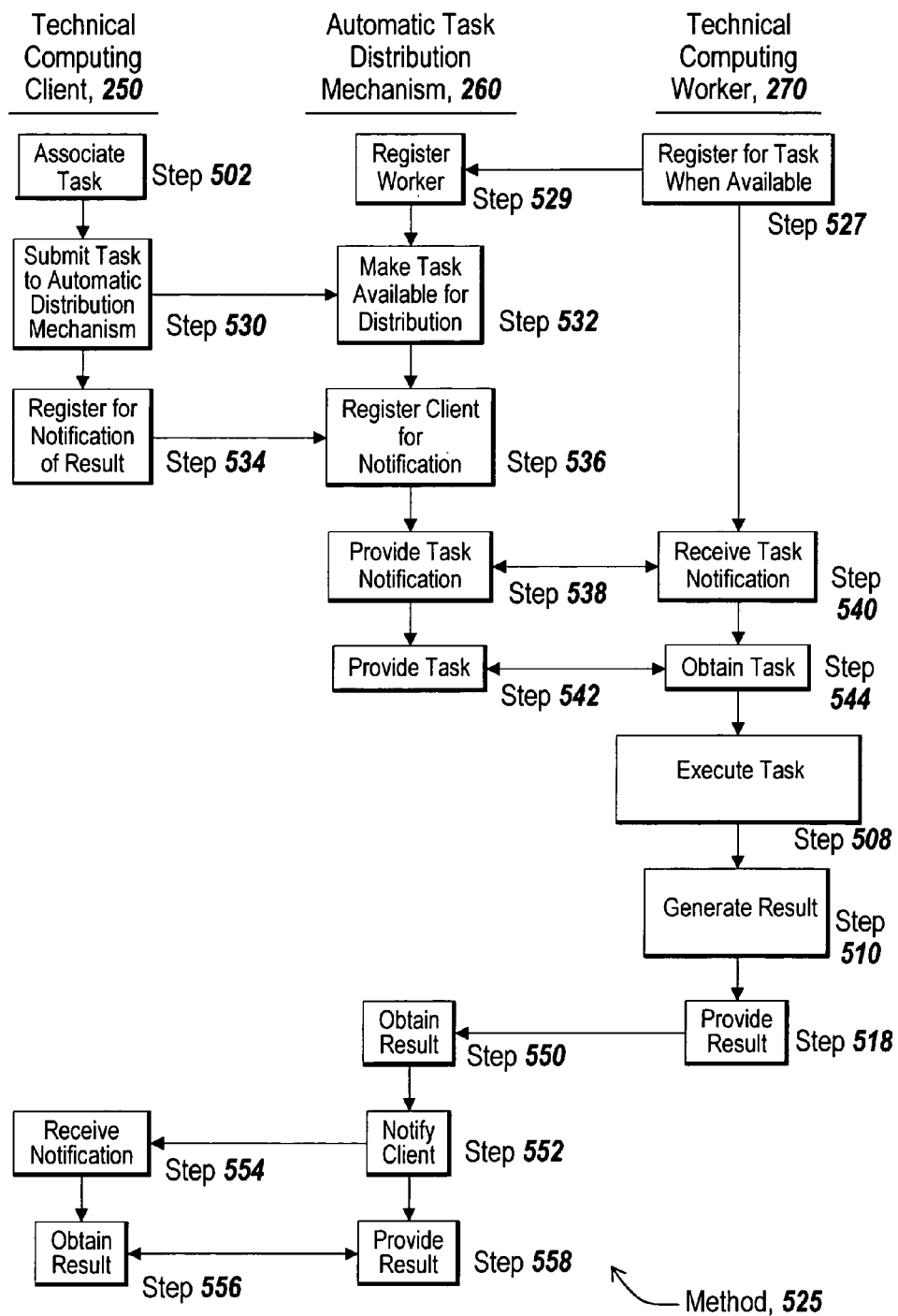
FIG. 5B is a flow diagram of steps performed in an embodiment of FIG. 3B.
Figure 5C:
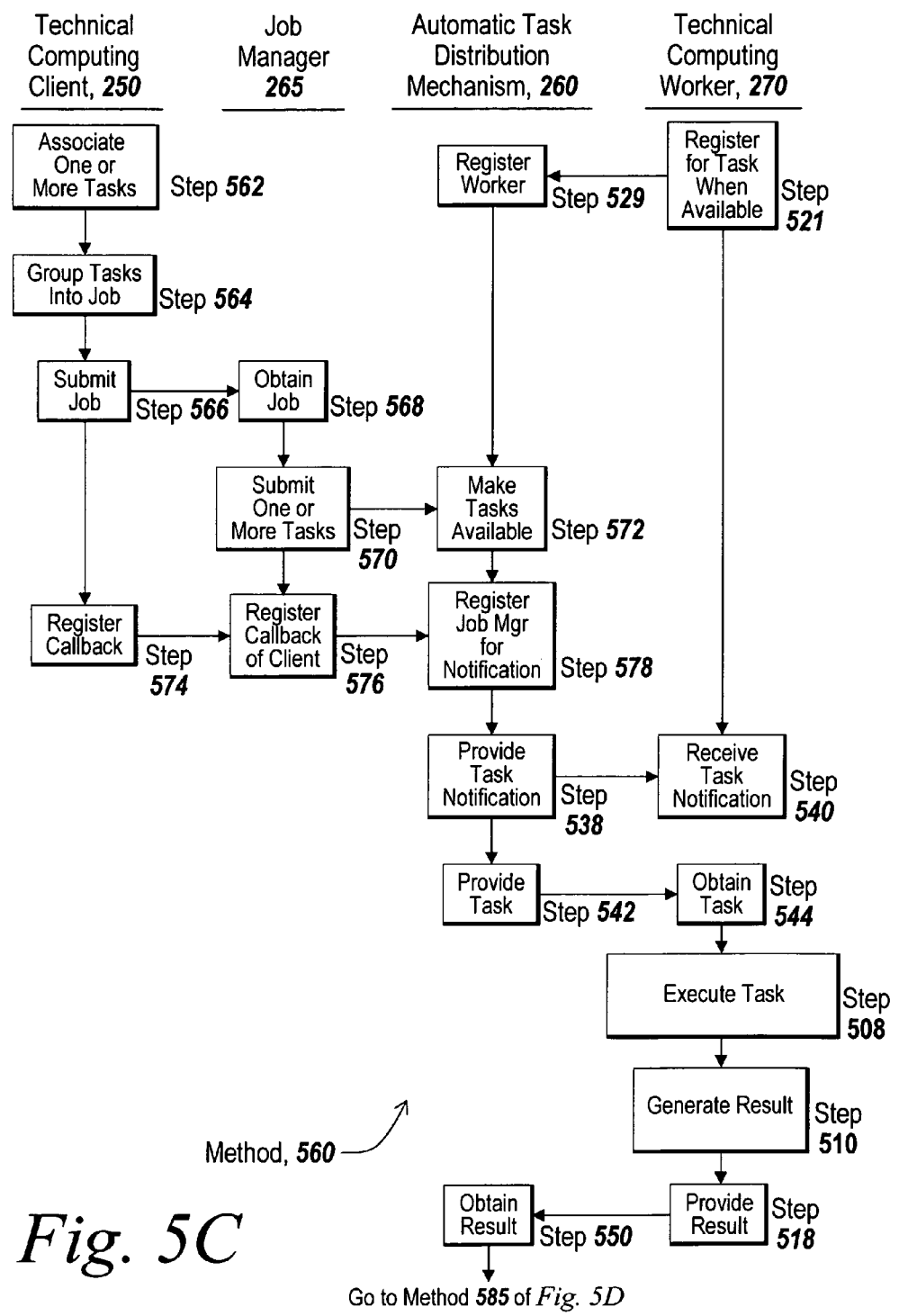
FIG. 5C and FIG. 5D are flow diagrams of steps performed in a batch mode of operations of the present invention.

In another aspect, the present invention relates to methods for distributing the simulation of chemical or biological processes or reactions to technical computing workers 270A-270N for processing, either directly, or indirectly and automatically, as described above in reference to the embodiments depicted in FIGS. 3A-3C. FIGS. 5A, 5B and 5C each show a flow diagram of the methods of the three modes of distribution. FIG. 5A depicts the method of direct distribution, FIG. 5B, the method of an automated distribution, and FIG. 5C, a batch mode method of automated distribution.

Referring now to FIG. 5A, one embodiment of the method 500 to distribute a task from a technical computing client 250 to a technical computing worker 270 is illustrated. Method 500 is practiced with the direct distribution embodiment of the invention depicted in FIG. 3A. On the technical computing client 250 a task is associated with a chemical reaction to be simulated (step 502). The task defines a function, command or operation, such as may be available in the programming language of MATLAB®, and the number of arguments and input data of the arguments. The technical computing client 250 then submits the task (step 504) to the technical computing worker 270. The technical computing worker 270 receives the task (step 506) and performs the requested technical computing as defined by the task (step 508). In performing the technical computing on the task, an associated result may be generated (step 510). In alternative embodiments, either no result is generated, or no result is required to be returned to the technical computing client 250. After generating the result of the task, the technical computing worker 270 provides the result (step 512) to the technical computing client 250, and the technical computing client 250 obtains the result from the technical computing worker 270 (step 514).

Referring now to FIG. 5B, an embodiment of the method 525 of simulating a chemical process or reaction in a distributed technical computing environment is illustrated. Method 525 is practiced with the automatic task distribution embodiment of the invention depicted in FIG. 3B. A technical computing worker 270 registers to receive notification of one or more tasks (step 527) becoming available, or appearing, in the automatic task distribution mechanism 260. On the technical computing client 250 a task is associated with a chemical process or reaction to be simulated (step 502). The technical computing client 250 then submits the task (step 530) to the automatic task distribution mechanism 260. The automatic task distribution mechanism 260 receives the task and makes the task available for distribution (step 532) to a technical computing worker 270. The technical computing client registers (step 534) with the automatic task distribution mechanism 260 to receive notification when a result associated with the task submitted in step 530 is available, or appears, in the automatic task distribution mechanism 260. The automatic task distribution mechanism 260 registers the technical computing client 250 for notification when the result appears (step 536). The automatic task distribution mechanism 260 provides notification (step 538) to the technical computing worker 260 of the availability of the task. In response to receiving the notification (step 540), the technical computing worker obtains (step 544) the task provided (step 540) from the automatic task distribution mechanism 260. The technical computing worker 270 performs the task (step 508). In performing the task, an associated result may be generated (step 510). In alternative embodiments, either no result is generated or the result is not required to be returned to the technical computing client 250. After generating the result from computing the task (step 510), the technical computing worker 270 provides the result (step 512) to the automatic task distribution mechanism 260. After obtaining the result from the technical computing worker 250 (step 550), the automatic task distribution mechanism 260 notifies (step 552) the technical computing client 250 that the result is available. The technical computing client 250 obtains (step 556) the result provided (step 558) by the automatic task distribution mechanism 260.

Figure 5D:
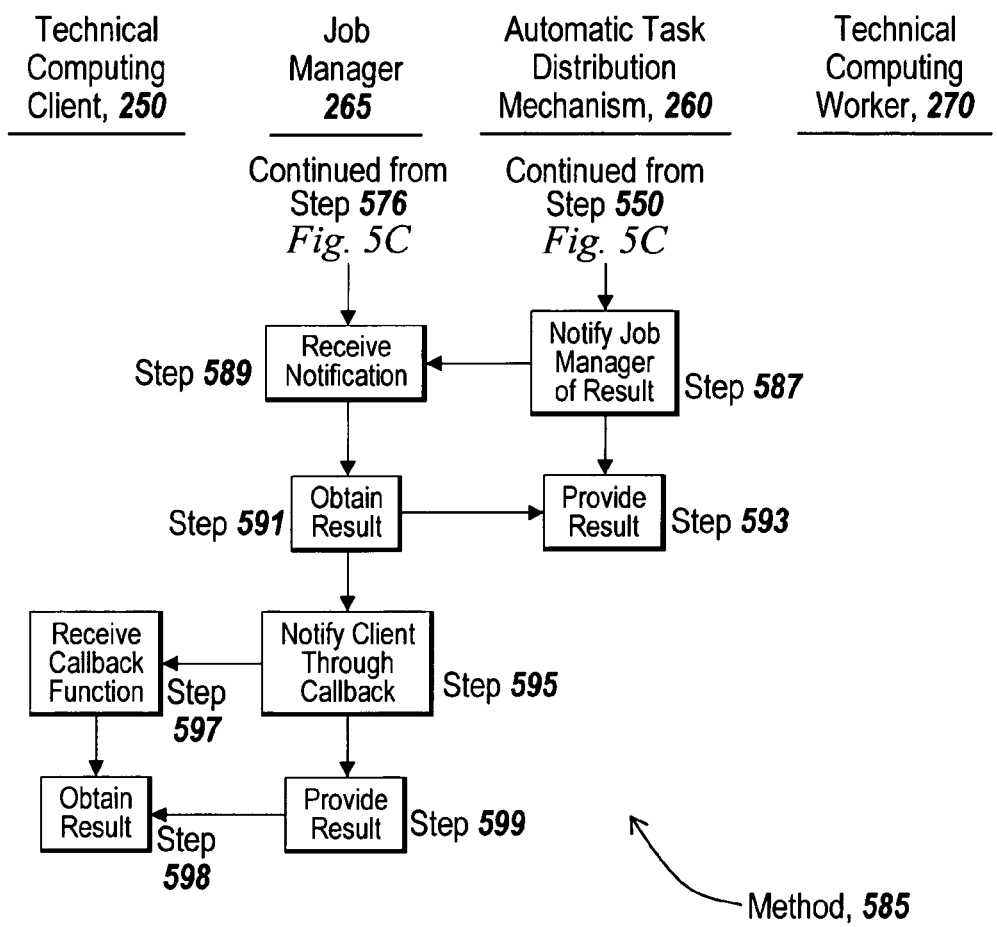

Referring now to FIGS. 5C and 5D, one embodiment of the method 560 to distribute a task from a technical computing client 250 to a technical computing worker 270 in a batch mode of operation is illustrated. Method 560 is practiced with the batch mode of the automatic task distribution system (e.g. 315 or 320). A technical computing worker 270 registers to receive notification of one or more tasks (step 527) becoming available, or appearing, in the automatic task distribution mechanism 260. In an exemplary embodiment, the technical computing worker registers to receive a task from the job manager 265 or automatic task distribution mechanism 260 as notification to perform computing on the task. On the technical computing client 250 one or more tasks are associated with a chemical reaction to be simulated (step 562). The technical computing client 250 groups one or more tasks of the tasks into a job associated with the chemical reaction to be simulated (step 564). The technical computing client 250 then submits the job (step 566) to the job manager 265. The job manager 265 obtains the job (step 568) from the technical computing client 250 and provides the one or more tasks of the job (step 570) to the automatic task distribution mechanism 260, which makes the one or more tasks available for distribution (step 572) to one or more technical computing workers 270A-270N. In an exemplary embodiment, the job manager 265 or the automatic task distribution mechanism 260 may submit the one or more tasks to the one or more technical computing workers 270A-270N. In another embodiment, the technical computing worker 270 may take the task from the job manager 265 or the automatic task distribution mechanism 260.

The technical computing client 250 registers (step 574) a callback function with the job manager 265. The technical computing client 250 may setup and/or register other callback functions based on changes in the state of processing of a task or job, or changes in the state of the job manager, or other events available to trigger the calling of a function. The job manager 265 calls this function when the job is completed, i.e., when each of the one or more tasks of the job have been completed. In turn, the job manager 265 may register (step 576) with the automatic task distribution mechanism 260 to receive notification of the results of the submitted tasks appearing in the automatic task distribution mechanism 260, or being received from the technical computing worker 270A-270N. In one embodiment, the automatic task distribution mechanism 260 registers the notification request of the job manager (step 578). Then, the automatic task distribution mechanism 260 provides notification to the technical computing worker 270 of the availability of the task (step 538). In an exemplary embodiment, the task is sent, by the job manager 265 to the technical computing worker 270 as notification to perform the task. In response to receiving the notification or the task (step 540), the technical computing worker 270 obtains (step 542) the task provided (step 540) from the automatic task distribution mechanism 260 or the job manager 265. The technical computing worker 270 executes the task (step 508). In executing the task, an associated result may be generated (step 510). In alternative embodiments, either no result is generated or the result is not required to be returned to the technical computing client 250. After generating the result from computing the task (step 510), the technical computing worker 270 provides the result (step 510) to the automatic task distribution mechanism 260 or the job manager 265. After obtaining the result from the technical computing worker 250 (step 550), the automatic task distribution mechanism 260 notifies (step 587) the job manager 265 that the result is available. In an exemplary embodiment, the job manager 265 receives the results from the technical computing worker 270. In response to receiving the notification or the result (step 589), the job manager 265 obtains the result (step 591) provided by (step 593) the automatic task distribution mechanism 260. If the job manager 265 received the last result of the job, the job manager 265 will notify the technical computing client 250 that the job is completed via the registered callback function (step 595). After triggering the completed job callback function (step 597), the technical computing client 250 obtains (step 598) the result provided (step 599) by the job manager 265.

With the methods of simulation distribution described above (methods 500, 525, and 560) in view of the embodiment of the concurrent multiple distribution modes of operation depicted in system 400 of FIG. 4, one ordinarily skilled in the art will recognize the application of the above methods to the multiple modes of operation for each technical computing client 250A-250N in FIG. 4.

In similar fashion, biological systems having multiple chemical reactions can be simulated by, on the technical computing client 250, associating a job with the biological system to be simulated. The job comprises multiple tasks associated with the chemical reactions of the biological system. The technical computing client 250 then submits the job to the job manager 265. The job manager 265 obtains the job from the technical computing client 250 and provides the one or more tasks of the job to the automatic task distribution mechanism 260, which makes the one or more tasks available for distribution to one or more technical computing workers 270A-270N.

Figure 6A:
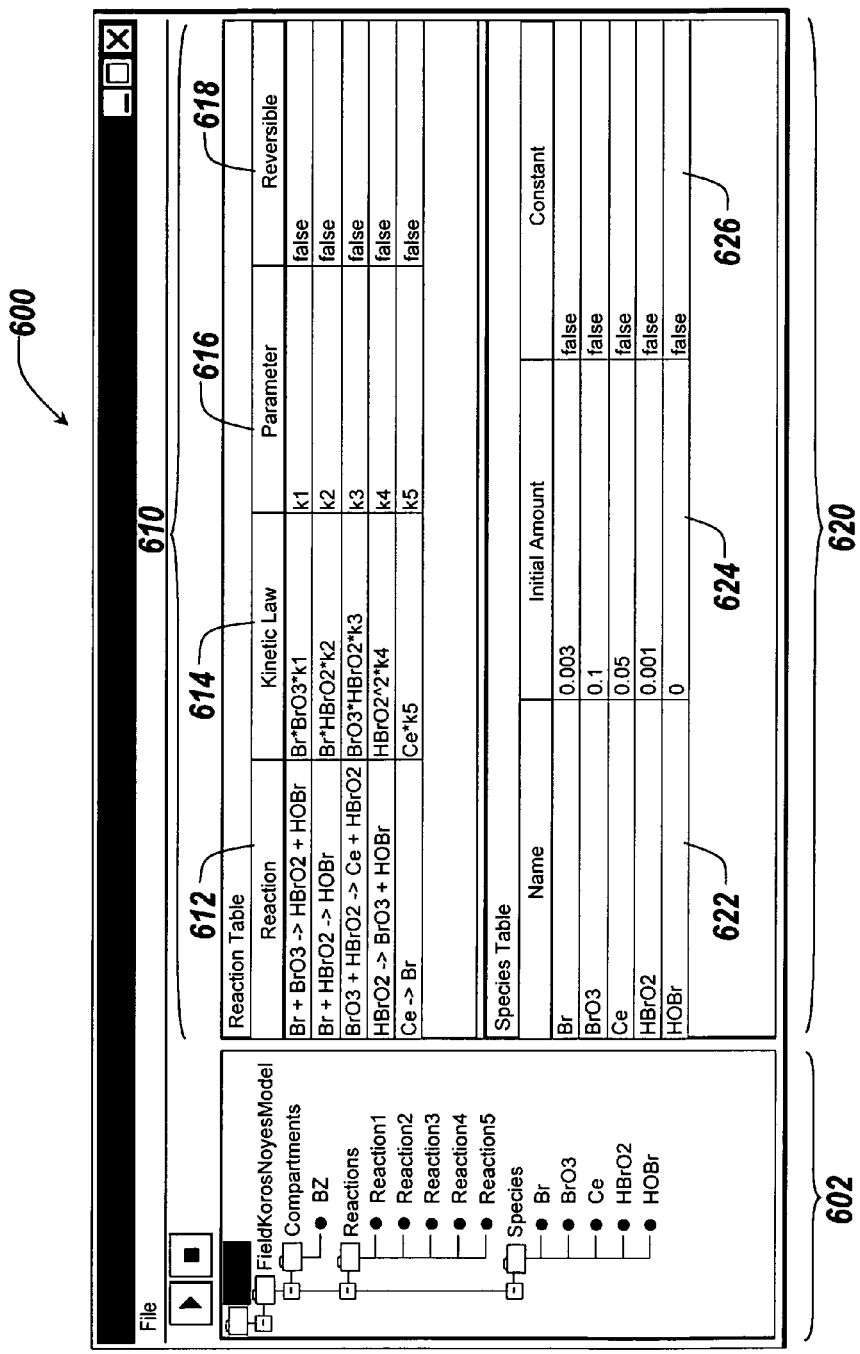
FIG. 6A is a screenshot depicting one embodiment of a tabular modeling environment.
Figure 6B:
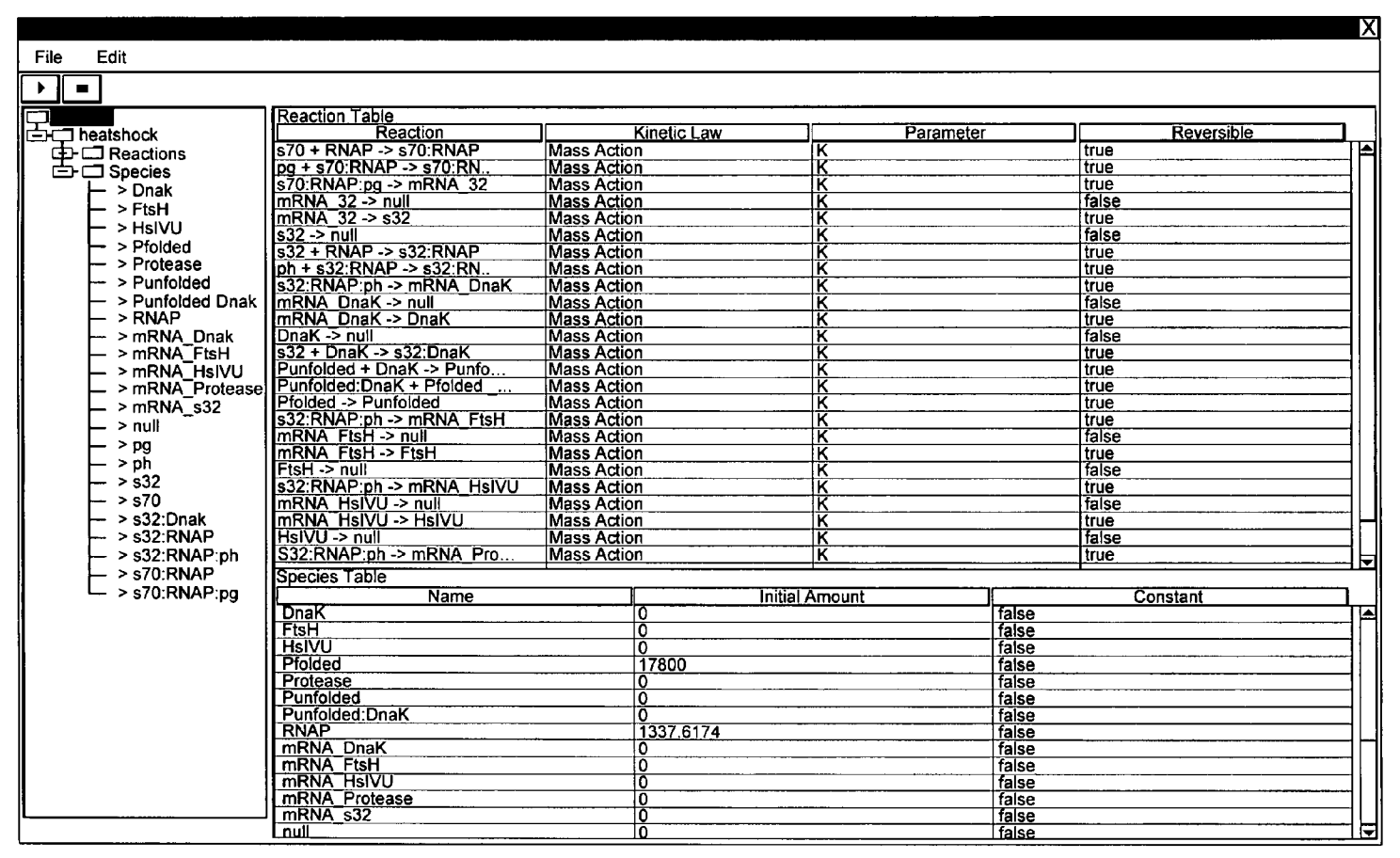

In certain embodiments, a user may model a chemical reaction using a graphical user interface (GUI). An example of this can be seen in FIGS. 6A and 6B. FIGS. 6A and 6B depict an embodiment of a tabular graphical user interface 600 that may be used to receive input manufactured by a user for creating a model. As shown in FIGS. 6A and 6B, the user interface may include a model pane 602. In the embodiment shown in FIGS. 6A and 6B, the model pane 602 lists one or more models in a tree structure familiar to users of computers operating under control of an operating system, such as the WINDOW operating system manufactured by Microsoft Corp. of Redmond, Wash., or another suitable operating system using graphical controls. In the particular embodiment depicted by FIG. 6A, a single model of a chemical reaction is contained in the model pane 602, indicated by the folder labeled "FieldKorosNoyesModel". That model contains three subfolders: "Compartments"; "Reactions"; and "Species". The subfolders represent pieces of the modeled reaction. Other graphical user interface schemes may be used to present this information to the user. In some embodiments, the model pane 602 may display a number of folders representing models. User selection of a particular folder causes the system to display folder in the model pane 602 that represent pieces of the reaction, e.g., compartments, reactions, and species. In still other embodiments, each model and all components of all models may be displayed in the model pane 602 and each model may be associated with a "radio button." Selection of the radio button associates with a model causes that model and its constituents to be actively displayed. In some of these embodiments, unselected models are displayed in grey type, or may have a transparent grey overlay indicating that they are not currently the active model.

The illustrative graphical user interface 600 also includes a reaction table 610, and a species table 620. The reaction table 610 is associated with the "Reactions" folder displayed in the model pane 602. Similarly, the species table 620 is associated with the "Species" folder displayed in the model pane 602. In some embodiments, collapsing the associated folder causes the table to not be displayed. The respective tables may be displayed in their own graphical user interface window, rather than in the same window as the graphical user interface 600, as shown in FIG. 6A.

The reaction table 610 lists each reaction present in a modeled biological process or chemical reaction. In the embodiment shown in FIG. 6A, the modeling environment 600 displays reactions present in the Field-Koros-Noyes model of the Belousov-Zhabotinsky reaction and includes four columns: a reaction column 612, a kinetic law column 614, a parameter column 616, and a reversible column 618. Each row of the reaction table 610 corresponds to a particular reaction. The number and format of columns displayed by the reaction table may be selected by the user. In other embodiments, the number and format of columns to be displayed may be based on the type of reaction selected by the user.

The reaction column 612 displays a reaction represented in an abstract format, e.g., Ce→Br. In other embodiments, the reaction may be represented as a differential equation, in stochastic format, or as a hybrid of two or more of these formats. In some embodiments, the reaction table includes a column identifying modifiers of the reaction. For example, some reactions can be catalyzed by a substance. This may be represented in the tabular format as Ce-m(s)→Br, meaning that the presence of the species "s" accelerates the conversion of Ce into Br.

In the embodiment shown in FIG. 6A, the reaction table 610 also includes a kinetic law column 614 which identifies the kinetic law expression the identified reaction follows. In the embodiment shown in FIG. 6A, the kinetic law associated with the Ce→Br reaction is "Ce*k5," meaning that Ce is consumed at a rate controlled by the parameter "k5" and the amount of Ce present. In the embodiment shown in FIG. 6A, the parameters for the kinetic law expression are listed in the parameter column 616. In some embodiments, the reaction table 610 includes a column identifying the name of the kinetic law associated with a particular reaction, e.g. "mass action" or "Michaels-Menten." In other embodiments, the reaction table 610 includes a column identifying the units in which the kinetic law parameters are expressed, e.g., 1/seconds, 1/(moles*seconds), etc.

Still referring to the embodiment shown in FIG. 6A, the reaction table 610 includes a reversible column 618, which indicates whether the associated reaction is reversible. A reversible reaction is one which occurs in either direction, i.e. Ce <-> Br. In some embodiments the reaction table 610 may include a column identifying dynamics of the reaction, e.g., "fast" or "slow." In some of these embodiments, the rapidity with which a reaction occurs is identified on a scale of 1 to 10. In still other embodiments, the user may be presented with a slide control that allows the rapidity of various reactions to be set relative to one another. In still further embodiments, the reaction table 610 may include a column for annotations or notes relating to the reaction.

The modeling environment 600 shown in FIG. 6A also displays a species table 620. In the embodiment shown in FIG. 6A, the species table 620 includes a name column 622, an initial amount column 624, and a constant column 626. The species table depicts the initial conditions and amounts of material used in the modeled biological process or chemical reaction. Thus, in the embodiment shown in FIG. 6A, the modeled biological process begins with 0.003 molar units of bromine, i.e., 0.003 multiplied by Avrogado's number. The constant column 626 is set to "true" if the model should assume that there is an infinite supply of a particular species. In other embodiments the species table 620 includes other columns such as a column identifying units (e.g., moles, molecules, liters, etc.), whether a particular species is an independent variable in the model (i.e., whether the species is an input to the system), a column for annotations, or a column for notes.

FIG. 6B depicts in tabular form reactions for simulating the *E. Coli* heat shock response model according to an illustrative embodiment of the invention. As described above in connection with FIG. 6A, the upper table displays the various reactions involved in transcription and translation of the heat shock proteins as well as the interactions of heat shock proteins with unfolded (or denatured) proteins. As depicted in FIG. 6B, all reactions in the *E. Coli* heat shock response model have mass action kinetics and some are reversible, while some are not. Another method of representing chemical or biochemical reactions is by way of a block diagram.

Figure 7:
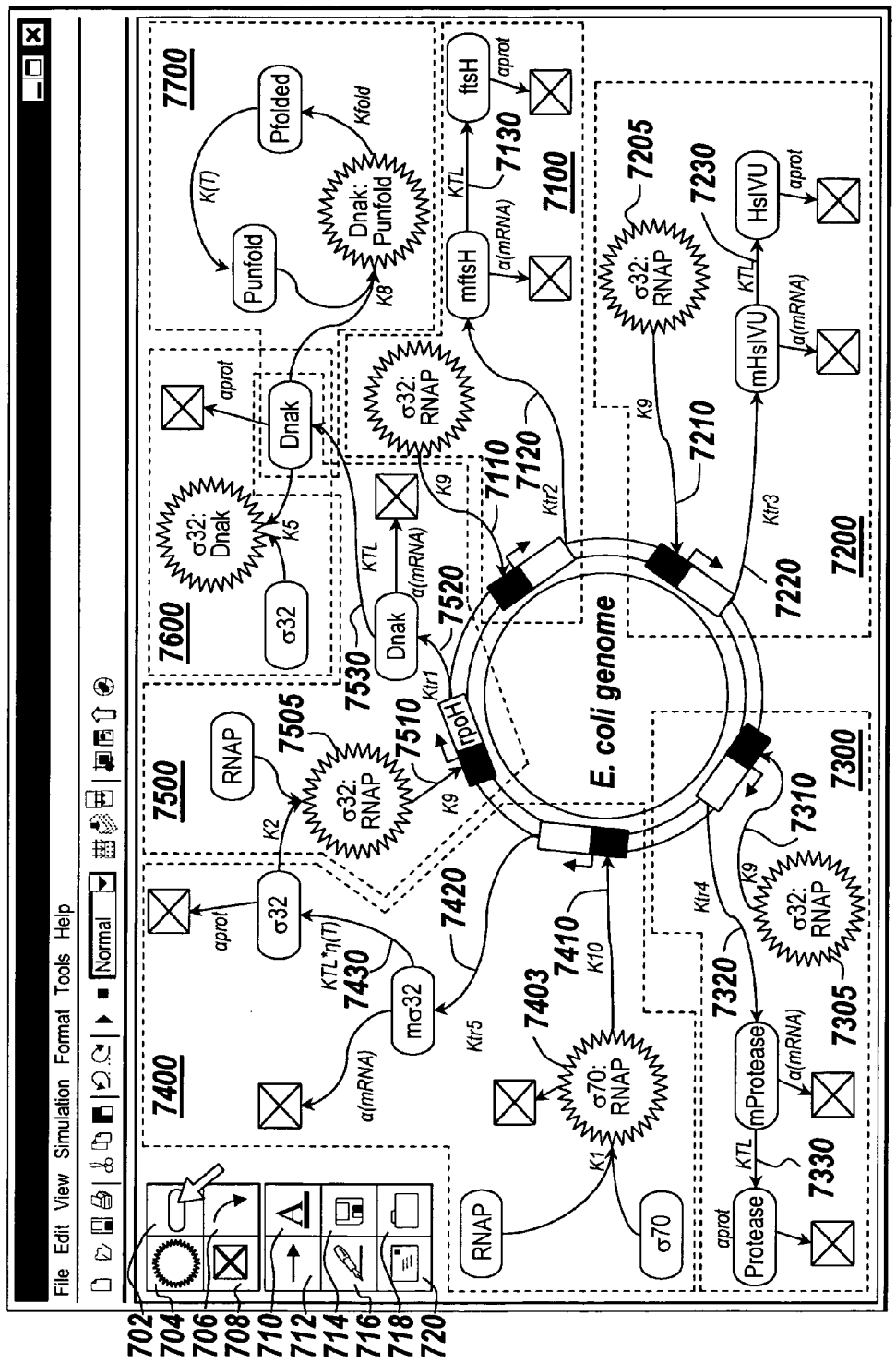
FIG. 7 is a screenshot of one embodiment of a graphical user interface that facilitates construction of block diagram representations of chemical reactions or biological processes.

In still other embodiments, the modeling environment 600 allows a user to represent a biological process or chemical reaction as a block diagram. FIG. 7 depicts an embodiment of a block diagram modeling environment. In the embodiment depicted in FIG. 7, a block diagram showing heat shock reaction in E. Coli bacteria is under construction. As is well known, heat shock response in E. coli is a protective cellular response to heat-induced stress. Elevated temperatures result in decreased E. coli growth, in large part, from protein unfolding or misfolding. The heat shock response, via heat shock proteins, responds to heat induced stress by refolding proteins via chaperones or by degrading nonfunctional proteins via proteases.

The block diagram shown in FIG. 7 depicts the expression of five particular gene sequences involved in the heat shock response. In part, FIG. 7 depicts pathways 7100, 7200, 7300 for the expression of proteases involved in heat shock response. Pathways 7100, 7200, 7300 represent the expression of heat shock proteins ftsH, Hs1VU and other proteases, respectively. The pathways 7100, 7200, 7300 are activated by the interaction 7105, 7205, 7305 of $\sigma^{32}$ with RNA polymerase at the promoter of the respective sequence. Each pathway 7100, 7200, 7300 depicts the transcription 7120, 7220, 7320 of the mRNA mediated 7110, 7210, 7310 by the $\sigma^{32}$ and RNA polymerase interaction 7105, 7205, 7305 at the promoter and the subsequent translation 7130, 7230, 7330 of the protease. The heat shock proteases, including ftsH and Hs1VU, serve to degrade proteins rendered nonfunctional by heat stress. Similarly, the diagram depicts the pathways 7400, 7500 involved in the expression of the heat shock proteins $\sigma^{70}$ and DnaK, respectively. The expression of the $\sigma^{32}$ protein is activated 7410 by the interaction 7403 of $\sigma^{70}$ and RNA polymerase at the promoter. The $\sigma^{32}$ mRNA is transcribed 7420 and, subsequently, $\sigma^{32}$ is translated 7430. In a closely related pathway 7500, the heat shock protein DnaK is translated. The interaction 7505 of $\sigma^{32}$ and RNA polymerase at the promoter activate 4510 the transcription 4520 of DnaK mRNA and, subsequently, the translation 7530 of DnaK. DnaK, in turn, may either interact 4600 with $\sigma^{32}$ so as to stabilize $\sigma^{32}$ or, alternatively, may refold 7700 the proteins unfolded by heat stress.

A block diagram editor allows users to perform such actions as draw, edit, annotate, save, and print out block diagram representations of dynamic systems. Blocks are the fundamental mathematical elements of a classic block diagram model. In some of these embodiments, the modeling environment includes two classes of blocks, non-virtual blocks and virtual blocks. Non-virtual blocks are elementary dynamic systems, such as the $\sigma^{32}$ and RNA polymerase interaction 7105, 7205, 7305. A virtual block may be provided for graphical organizational convenience and plays no role in the definition of the system of equations described by the block diagram model. For example, in the block diagram of the heat shock mechanism in E. Coli bacteria depicted in FIG. 7, gene transcription mediated by σ32 to produce proteins, represented by 7100, 7200, and 7300, may be represented as a single, virtual block. In this case the virtual block adds hierarchy to a model for the purpose of improving the readability of models.

The block diagram editor is generally a graphical user interface (GUI) component that allows drafting of block diagram models representing a chemical or biochemical reaction by a user. FIG. 7 depicts an embodiment of a GUI for a block diagram editor that features a floating element palette. In the embodiment shown in FIG. 7, the GUI tools include various block tools 702, 704, 708, various wiring line connection tools 706, 712, an annotation tool 716, formatting tool 710, a save/load tool 714, a notification tool 720 and a publishing tool 718. The block tools 702, 704, 708 represent a library of all the pre-defined blocks available to the user when building the block diagram. Individual users may be able to customize this palette to: (a) reorganize blocks in some custom format, (b) delete blocks they do not use, and (c) add custom blocks they have designed. The blocks may be dragged through some human-machine interface (such as a mouse or keyboard) on to the window (i.e., model canvas). The graphical version of the block that is rendered on the canvas is called the icon for the block. There may be different embodiments for the block palette including a tree-based browser view of all of the blocks. In these embodiments, the floating element palette allows a user to drag block diagram elements from a palette and drop it in place on the screen. In some of these embodiments, there may also be a textual interface with a set of commands that allow interaction with the graphical editor. For example, dragging a polymerase block to the model may cause the system to prompt the user for the protein to be used in the polymerase reaction.

As one can see from FIGS. 6A, 6B, and 7 a model of a biological or chemical reaction, such as the heat shock response in E. Coli bacteria, can involve several reactions or processes. The simulation of these reactions can be expedited by divided them up into tasks, grouping the tasks into jobs and providing the jobs for distribution and execution on a distributed system.

Figure 8:
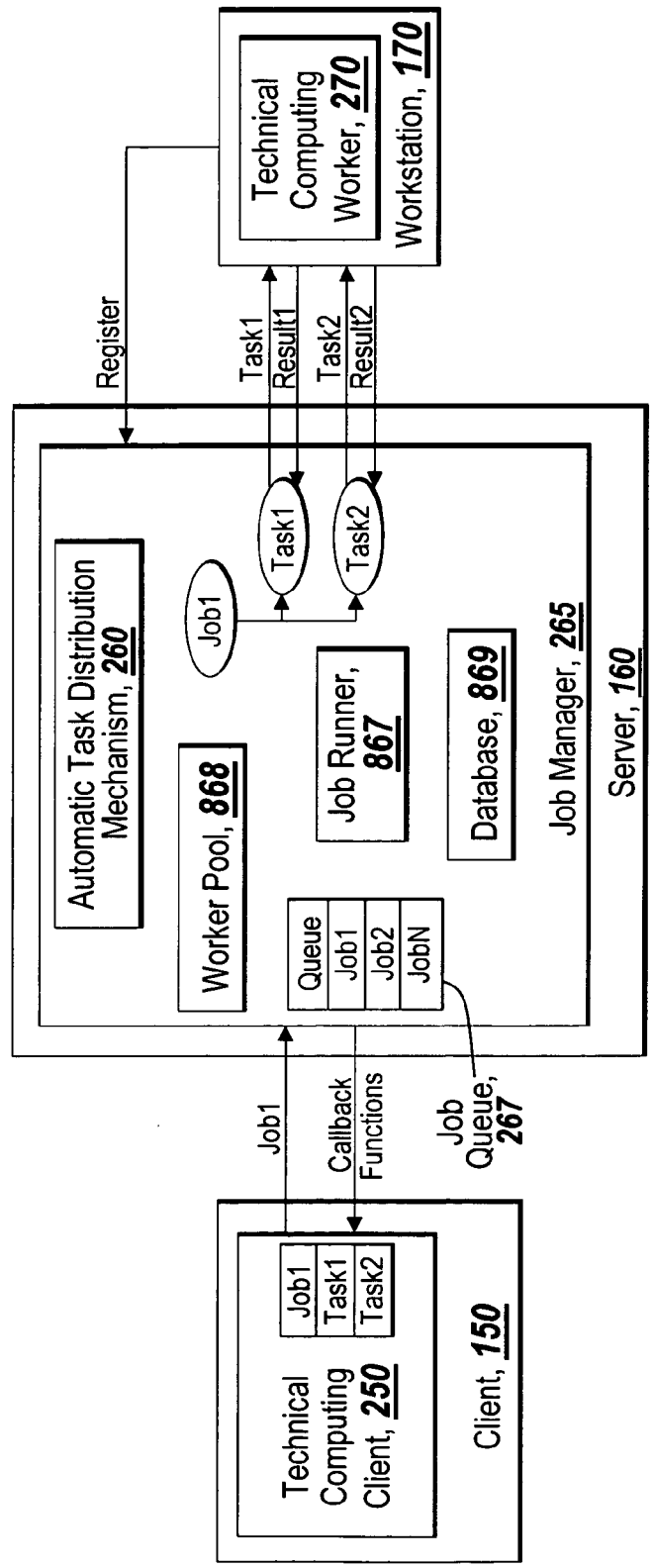
FIG. 8 is a block diagram depicting the details of a job manager comprising the automatic task distribution mechanism.

FIG. 8 depicts an exemplary embodiment of details of the batch mode of operation of the present invention using a database. In this embodiment, the job manager 265 includes the functionality of the automatic task distribution mechanism 260. In brief overview, the technical computing client 250 is in communication with the job manager 265, which is in communication with the technical computing worker 270. The job manager comprises a job queue 267, an automatic task distribution mechanism 260, a job runner 867, a worker pool 868 and a database 869. Any of these components of the job manager 265 can be a separate library, interface, software component or application. In an exemplary embodiment, these components can be running in their own processing thread to provide multi-tasking capabilities.

The worker pool 868 contains a list of technical computing workers 270A-270N that are available to work on a task. These technical computing workers 270A-270N may on startup register with a job manager 265. The name of the job manager 265 the technical computing worker 270A-270N is associated with may be configurable by an interface of the technical computing worker 270A-270N, or by a command line startup parameter, or an external configuration or registration file. The worker pool 868 may keep a list of "good" technical computing workers 270A-270N, or those workers to which the job manager 265 can communicate with and can determine has such a status to be available for processing tasks. The job manager 265 can update the worker pool 867 by going through the list of technical computing workers 270A-270N registered in the worker pool 867 and sending communications to each of the technical computing workers 270A-270N to determine their status and if they are available. Accordingly, the worker pool 867 can be updated to determine the current set of technical computing workers 867 available, or otherwise able to receive tasks from the job manager 265.

The job runner 867 is responsible for determining the next task to work on and for submitting the task to a technical computing worker 270A-270N. The job runner 867 works with the job queue 267 and takes the next task for processing from a job in the job queue 267. The job runner 867 obtains from the worker pool 868 a name of or reference to a technical computing worker 270A-270N and submits the task for processing to the obtained technical computing worker 270A-270N. The job runner 867 may be configured to have business rule logic to determine the next task to take from the job queue either in a FIFO manner supported by the job queue 267 or any other manner based on priority, availability, task and job option settings, user configuration, etc. The job runner 867 in conjunction with the worker pool 868 and the job queue 267 can form a portion of or all of the functionality of the automatic task distribution mechanism 260. The job runner 867 can have such logic to determine from the worker pool 868 which technical computing worker 270A-270N should be assigned and sent a task from the job queue 267. Alternatively, a separate automatic task distribution mechanism 260 can be responsible for determining the technical computing worker 270A-270N to be assigned a task and to send the task to the assigned technical computing worker 270A-270N. In any of these embodiments, the technical computing worker 250 does not need to know the identity, such as via a hostname or an interne protocol address, of the technical computing worker 270A-270N assigned to perform technical computing on a task.

The job manager 265 also has a database 869 for storing and retrieving job manager, job and task objects and data, or other objects and data to support the operations described herein. For example, jobs in the job queue 267, the list of workers of the worker pool 868, the tasks of any jobs in the job queue 267, the properties of any of the task, job or job manager objects may be stored in the database 869. The database 869 can be a relational database, or an object-oriented database, such as database software or applications from Oracle® or SQL Server from Microsoft®, or any other database capable of storing the type of data and objects supporting the operations described herein. The database 869 can be an in process database 869 of the job manager 265 or it can be a remote database 869 available on another computing device 102' or another server 260'. Furthermore, each instance of the job manager 265A-265N could use a different database and operating system than other instances of the job manager 265A-265N, or be using a local database while another job manager 265A-265N uses a remote database on another server 160'. One ordinarily skilled in the art will appreciate the various deployments of local or remote database access for each of the one or more job managers 265A-265N.

The job manager 265 can be configured to execute certain functions based on changes of the state of a job in the queue 267. For example, the technical computing client 250 can setup functions to be called when a job is created in a job queue 267, when the job is queued, when a job is running or when a job is finished. The job manager 265 is to call these functions when the appropriate change in the state of job occurs. In a similar manner, the task and job can be configured to call specified functions based on changes in state of the task or job. For example, a job may be configured to call a function when a job is added to the queue, when a task is created, when a task is completed, or when a task starts running. A task may be configured to call a function when the task is started, or running.

Referring still to FIG. 8, the technical computing client 250 submits a job, Job1, comprised of one or more tasks, such as Task 1 and Task2, to the job manager 265. The job manager receives the job, e.g., job1, and places the job into a job queue 267. The job runner 867 then obtains the one or more tasks from the first job submitted to the job queue 267. A technical computing worker 270 registers with the job manager 265 and is listed in the worker pool 668 of the job manager 265. From the worker pool 868, the job runner 867 determines a technical computing worker 270A-270N to submit the task for processing. The technical computing worker 270A-270N obtains the function to be executed from the definition of the function in data structure of the task object, performs the function and generates a result of the function for the task. Then the technical computing worker 270 updates the task object to provide a result of the task. For example, the task object may have a field representing the output arguments from the execution of the function defined by the task. The output arguments may contain one or more arrays of data as allowed by the programming language of MATLAB®. Additionally, the task object may contain an error field to which the technical computing worker 270A-270N updated to indicate any error conditions in performing the task or executing the function of the task. The job manager 265 checks to see if this is the last result to be obtained from a technical computing worker 270A-270N for the job currently being processed. If the result is the last result, the job manager 265 can provide the set of task results for the completed job to the technical computing client 250.

The MATLAB® programming enables you to write a series of MATLAB® statements into a file, referred to as an M-File, and then execute the statements in the file with a single command. M-files can be scripts that simply execute a series of MATLAB® statements, or they can be functions that also accept input arguments and produce output. Furthermore, the MATLAB® programming language enables the association of a callback function with a specific event by setting the value of the appropriate callback property. A variable name, function handle, cell array or string can be specified as the value of the callback property. The callback properties for objects associated with Simulation distribution software are designed to accept any of the above described configurations as the value of the callback property, and may accept any other command, function or input parameter value that are or may become available in the MATLAB® programming language. This allows users of the MATLAB® programming language to use the function calls they are familiar with, without learning the object-oriented mechanism, and take advantage of the distributed processing of tasks offered by Simulation distribution software of the present invention.

Figure 9:
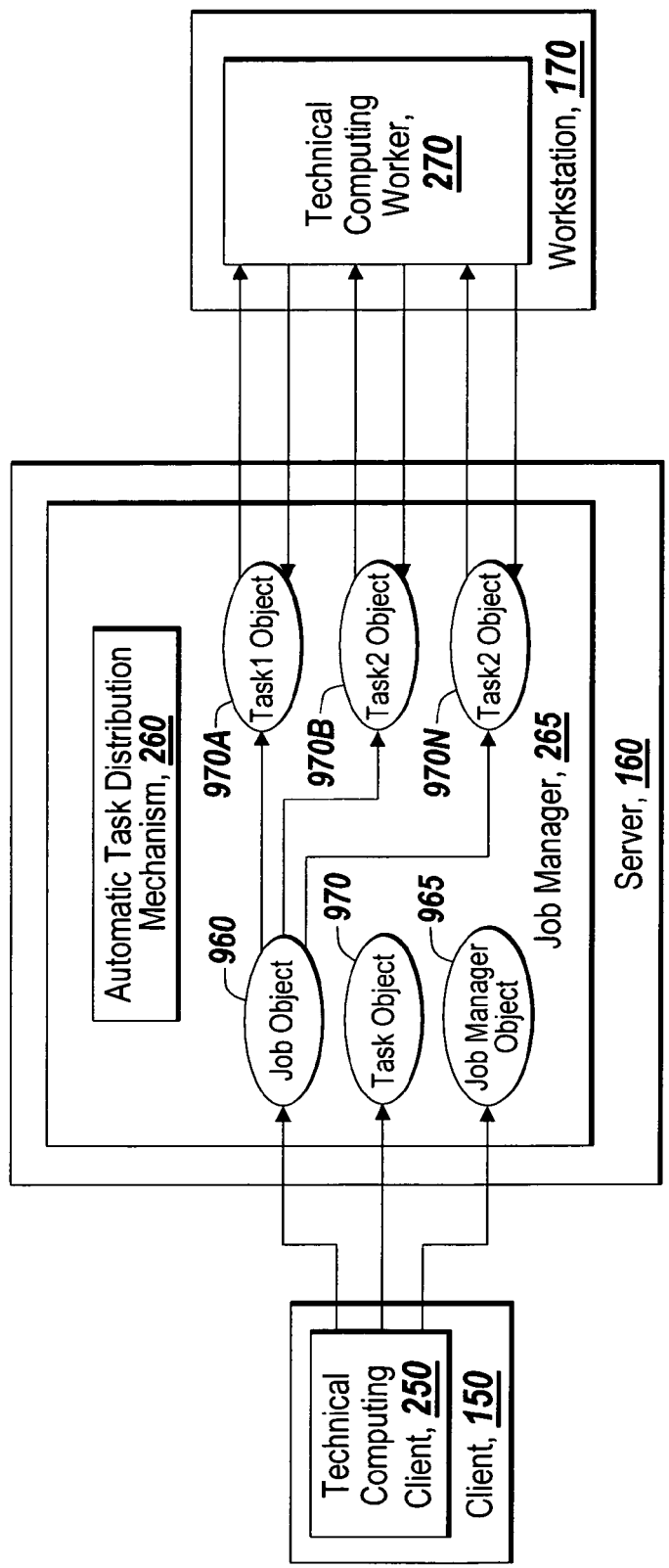
FIG. 9 is a block diagram illustrating the use of objects for user interaction with an exemplary embodiment of the distributed system.

In the exemplary object-oriented distributed system 905 of FIG. 9, the technical computing client 250 creates or declares a job object 760 residing in the job manager 265. The job object comprises one or more task objects 970A-970N. The job object 760 further defines properties associated with the job, such as those job properties described in further detail below. For example, a timeout property to specify the time limit for completion of a job. Additionally, the minimum and maximum number of technical computing workers to perform the tasks of the job can be set. The task object 970A-970N is an object that defines a function to be executed by a technical computing worker 270. The function contains a MATLAB® command, input data and number of arguments. The task object 970A-970N defines additional task properties, such as those defined below. For example, the task object 970A-970N may have a state property to indicate the current state of the task. Additionally, the technical computing client 250 may interface with the job manager 265 through a job manager object 965 residing on the job manager 265. In a similar manner to the job object 760 and task objects 970A-970N, the job manager object 965 may have properties to define configuration and other details about the job manager 265 as described below. For example, the job manager object 965 may have a hostname property to indicate the name of the computer where a job queue exists, or a hostaddress property to indicate the internet protocol address of the computer. For any of the job manager object 965, job object 960 or task objects 970A-970N, the technical computing client may not instantiate a local object but may just have a proxy or facade object to reference the object existing in the job manager 265.

Still referring to FIG. 9, the technical computing client 250 submits the job to the job manager 265 via the job object 965. The job manager 265 obtains each of the task objects 970A-770N from the job object 965. The job manager puts the job of the job object 960 into the job queue 267. The job runner 867 obtains the one or more task objects 970A-970N from the job object 960. The job runner 867 with the worker pool 868 determines a technical computing worker 270 to process a task. The job runner 867 then submits a task, via a task object 970A-770N to an assigned technical computing worker 270. The technical computing worker 270 obtains the function to execute from the properties of the task object 970A-970N and performs technical computing of the task in accordance with the function. The technical computing worker 270 then obtains the results of the function and updates one or more properties of the task object 970A-970N with information about the results. In the case of any errors, the technical computing worker 270 may update any error properties of the task object 970A-970N. In a similar manner as the technical computing client 250, the technical computing worker 270 may use proxy or facade objects to interface with the job 960, job manager 965 or task 970A-970N objects residing in the job manager 265. The job manager 265 then updates the job object 960 with updated task objects 970A-970N containing the results of each task. The job manager 265 may also update other properties of the job object 760, such as start and finish times of the job, to reflect other information or status of the job. The job manager 265 then provides the updated job object 760 to the technical computing client 250. The technical computing client 250 then can retrieve the results of each task from the updated job object 960. One ordinarily skilled in the art will recognize the various combinations of uses of the properties and functions of these objects in performing the operations described herein and in support of any of the multiple modes of distribution as depicted in FIG. 4.

In an exemplary embodiment of the invention as depicted in FIG. 9 and by way of example, the follow provides an example of simulating a reaction in which one reactant exponentially decays into a product, i.e. X→Z. A Stochastic Simulation Algorithm (SSA) is used for the simulation. The steps for setting such a distributed simulation and plotting the results are set forth below.

```
Job manager
    jm=findResource('jobmanager','name','Shrikants_JM');
Job
    job=createJob(jm);
Tasks in the job
    numruns=5;
    for i=1:numruns
        task=createTask(job, 'expdecay', 2, {'ssa'});
    end
Capture command window output
    alltasks=get(job, 'Tasks');
    set(alltasks, 'CaptureCommandWindowOutput', true);
File Dependencies
    set(job,'FileDependencies',{'P:
        \Shrikant_Savant\sharedemo_scripts\dexpdecay\
        expdecay.m'});
Submit job
    submit(job);
Wait for results to complete
    waitForState(job);
Capture output messages
    outputmessages=get(alltasks, 'Command WindowOutput');
Get all the results
    results=getAllOutputArguments(job);
```

| Plot |
| --- |
| figure(2);<br>hold on;<br>for i = 1:numruns<br>    plot(results {i,1},results {i,2});<br>end<br>legend('X','Z');<br>title('Exponential Decay: X -> Z');<br>xlabel('Time: sec');<br>ylabel('Chemical Species Concentration: No. of Molecules');<br>axis([0 1 0 100]);<br>grid on; |

Figure 10A:
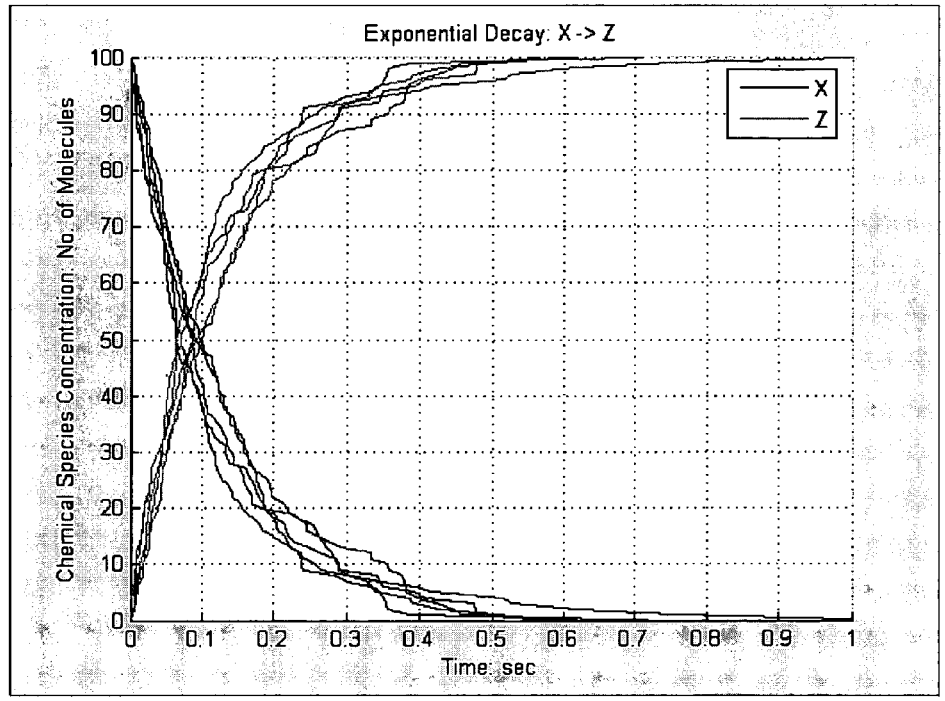
FIG. 10A is plot of results obtained by a distributed simulation of a chemical reaction using an object oriented interface of one embodiment.

The results of the distributed simulation can be seen in FIG. 10A. In this example, the M-file called is expdecay.m. The contents of this M-File are shown below.

```
%
% File: expdecay.m
%
% May 2004
%
% Reactions:
% x -> z
%
    function [t x] = expdecay(solver)
    if (nargin == 0)
        solver = '';
    end
    tfinal = 3.0; %2.5
    logdec = 1;
    errortol = 0.05;
    if (strcmpi(solver,''))
        solver = 'ssa'; % Default value
    end
    % Initial amounts and rates
    x0 = 100;
    z0 = 0;
    rateconst = 8;
    % Model
    m = sbiomodel('Exponential Decay');
    % Reactions
    reaction1 = addreaction(m, 'x -> z');
    klaw1 = reaction1.addkineticlaw('MassAction');
    % Species
    m.species(1).InitialAmount = x0;
    m.species(2).InitialAmount = z0;
    % Reactions
    rate1 = addparameter(reaction1 , 'k', rateconst);
    klaw1.K = rate1;
    % Random state
    clk = clock;
    rstate = fix(sum(clk(end-1:end)));
    % Simulate
    if strcmpi(solver, 'ssa')
        [t x] = sbiosimulate(m, solver, tfinal, logdec);
    elseif strcmpi(solver, 'explTau')
        [t x] = sbiosimulate(m, solver, tfinal, logdec, errortol);
    elseif strcmpi(solver, 'implTau')
        [t x] = sbiosimulate(m, solver, tfinal, logdec, errortol);
    end
%eof
```

In addition to the object-oriented interface to task and job management functionality of the distributed system, the programming language of Simulation distribution software may also support task distribution via high-level functional procedure calls. The MATLAB® programming language includes procedural function calls such as eval( ) and feval( ) that provide a quick and powerful procedure to execute functions. Additionally, the MATLAB® programming language supports anonymous functions and function handles. Function handles are useful when you want to pass your function in a call to some other function when that function call will execute in a different workspace context than when it was created. Anonymous functions give you a quick means of creating simple functions without having to create M-files each time and can be viewed as a special subset of function handles. An anonymous function can be created either at the MATLAB® command line or in any M-file function or script. Anonymous functions also provide access to any MATLAB® function. The @ sign is the MATLAB® operator that constructs a function handle or an anonymous function, which gives you a means of invoking the function. The MATLAB® programming language enables the association of a callback function with a specific event by setting the value of the appropriate callback property. A variable name, function handle, cell array or string can be specified as the value of the callback property. The callback properties for objects associated with Simulation distribution software are designed to accept any of the above described configurations as the value of the callback property, and may accept any other command, function or input parameter value that are or may become available in the MATLAB® programming language. This allows users of the MATLAB® programming language to use the function calls they are familiar with, without learning the object-oriented mechanism, and take advantage of the distributed processing of tasks offered by Simulation distribution software of the present invention.

An example of this, wherein three stochastic solvers-SSA, Explicit Tau, and Implicit Tau Leaping are used is provided below.

Figure 10B:
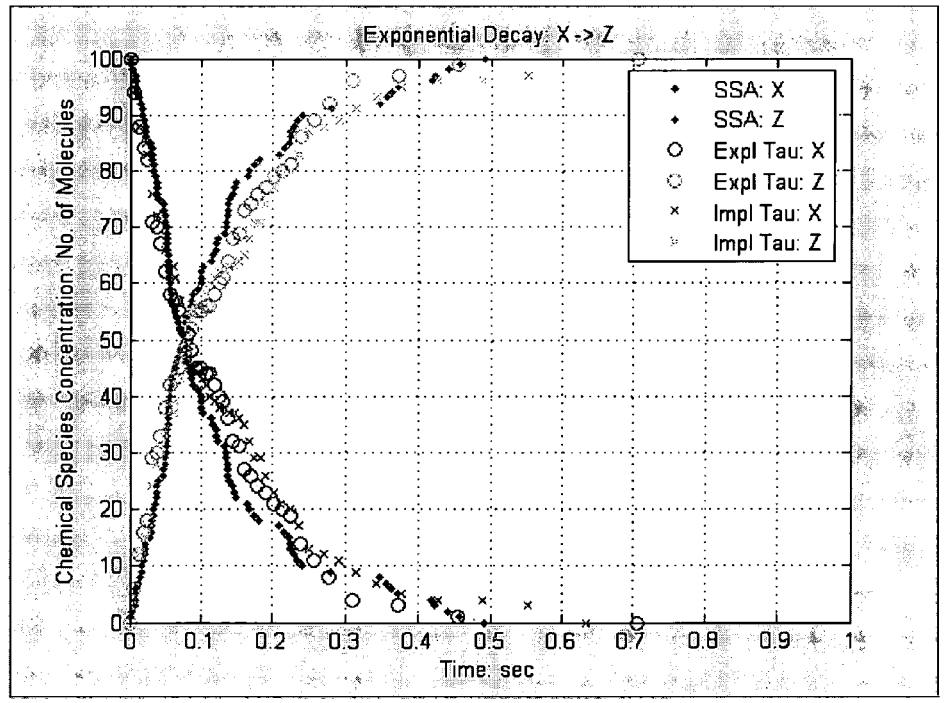
FIG. 10B is plot of results obtained by a distributed simulation of a chemical reaction using functional procedure calls of one embodiment.

Call dfeval
    [T X]=dfeval(@expdecay, {'ssa','expltau','impltau'}, 'JobManager','Shrikants_JM');

Plot results
    figure(3);
    plot(T{1},X{1},'.',T{2},X{2},'o',T{3},X{3},'x')
    legend('SSA: X','SSA: Z','Expl Tau: X','Expl Tau: Z','Impl Tau: X', 'Impl Tau: Z');
    title('Exponential Decay: X→Z');
    xlabel('Time: sec');
    ylabel('Chemical Species Concentration: No. of Molecules');
    axis([0 1 0 100]);
    grid on;

The results of the distributed simulation can be seen in FIG. 10B.

In alternative embodiments, the object-oriented interfaces and/or functional procedures available in the programming language, may be available in one or more application programming interfaces, and may be available in one or more libraries, software components, scripting languages or other forms of software allowing for the operation of such object-oriented interfaces and functional procedures. One ordinarily skilled in the art will appreciate the various alternative embodiments of the above class definitions, class method and properties, package scope methods, functional procedures and programming instructions that may be applied to manage the distribution of tasks and jobs for distributed technical computing processing of the present invention.

From an overall perspective and in view of the structure, functions and operation of the system as described herein, the current invention presents many advantages for distributed, streaming and parallel technical computing processing systems. The system can handle a wide variety of user configurations from a standalone system to a network of two machines to a network of hundreds of machines, and from a small task granularity to an extremely large task granularity of parallel, and parallel and serial technical computing.

Figure 11A:
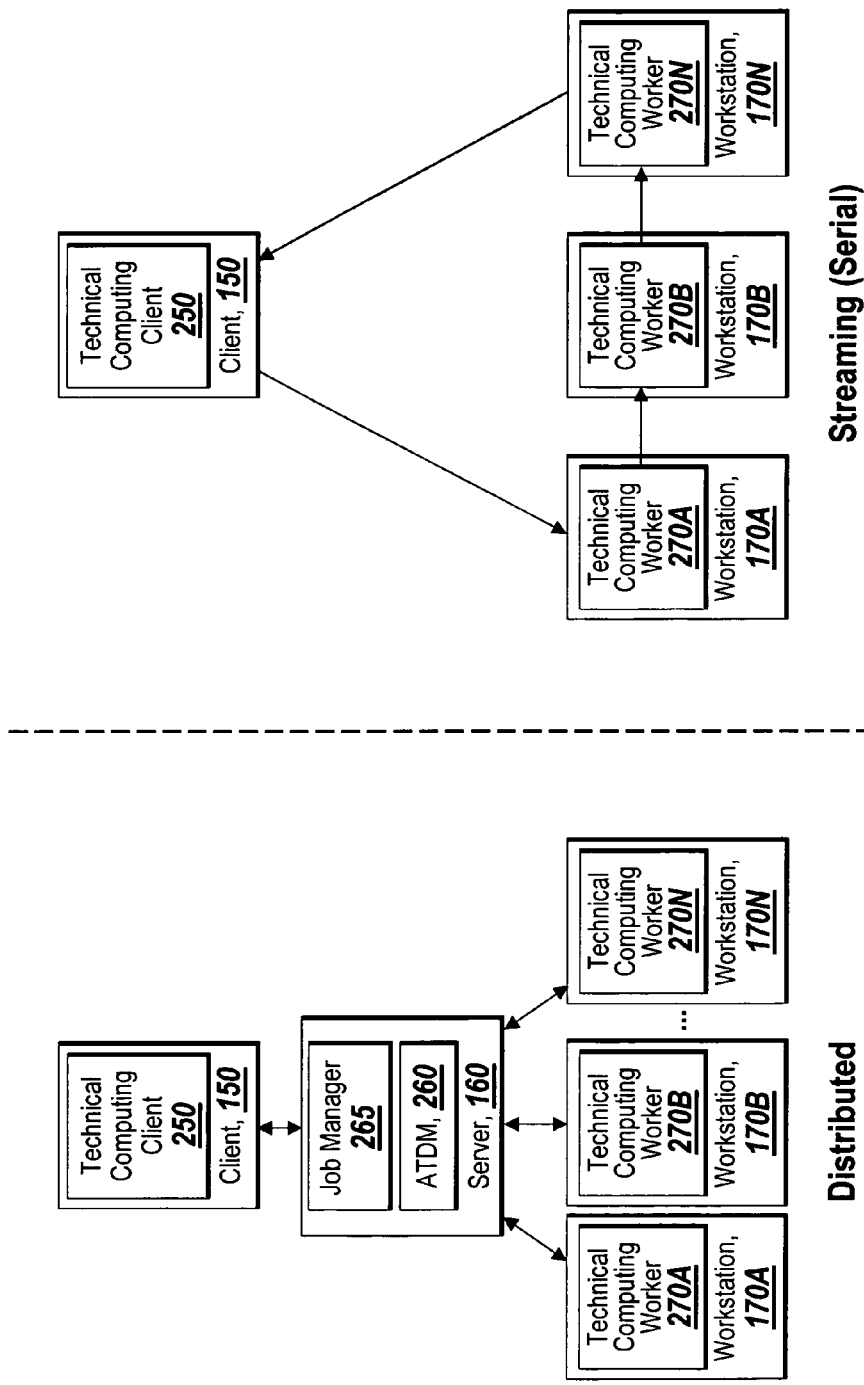
FIG. 11A is a block diagram illustrating an operation of the present invention for distributed and streaming technical computing.

Referring to FIG. 11A, the distributed system 1110 supports the delegation of tasks from a technical computing client 250 to remote technical computing workers 270A-270N leveraging the processing capability of each of the workstations 170A-170N hosting each of the technical computing workers 270A-270N. The tasks are executed independently of each other and do not require the technical computing workers 270A-270B to communicate with each other.

Still referring to FIG. 11A, the streaming, or serial, processing system 1110 allows serial processing to occur via multiple technical computing workers 270A-270N on multiple workstations 170A-170N. A technical computing client 250A submits a job requiring a task to be processed serially from technical computing worker 270A to technical computing worker 270B then to technical computing worker 270N. When technical computing worker 270A completes its technical computing of the task, technical computing worker 270A submits the task to technical computing worker 270B for further processing. In a similar fashion, the task can be submitted to additional technical computing workers 270N for further processing until the task is complete in accordance with its task definition. The last technical computing worker 270N to perform technical computing on the task submits the result to the technical computing client 250.

The streaming processing system 1120 can take advantage of specific workstations 170A-170N that may have faster processors for performing processor intensive portions of technical computing of the task or take advantage of technical computing workers 270A-270N with access to specific data sets or external control instrumentation as required for computation of the task.

Figure 11B:
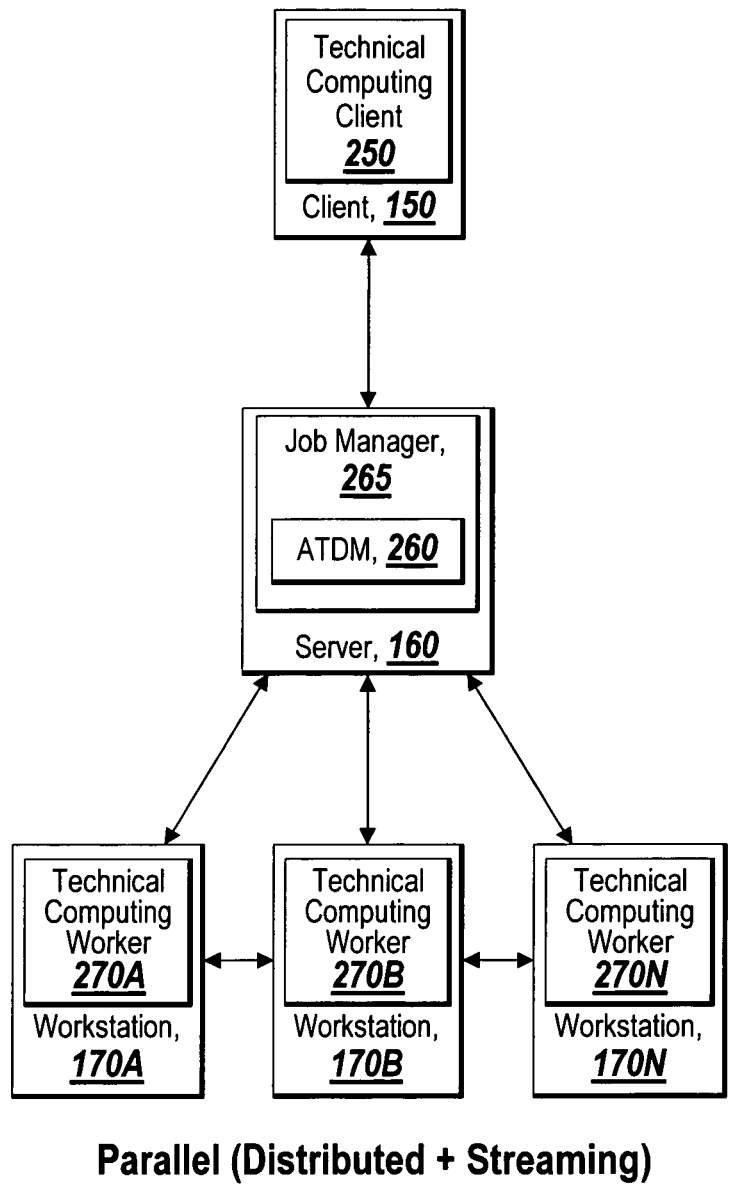
FIG. 11B is a block diagram illustrating an operation of the present invention for parallel technical computing.

In FIG. 11B, a parallel system 1130 is depicted which combines the distributed and streaming configuration of the systems (1100 and 1110) in FIG. 11A. In brief overview, technical computing workers 270A and 270B and 270N can be executing a set of tasks independently of each other. Additionally, these technical computing workers can then submit tasks to other technical computing workers to perform technical computing of a task in a streaming fashion. For example, technical computing worker 270A can submit a task for further processing to technical computing worker 270B, and in turn, technical computing worker 270B can submit the task for further processing by technical computing worker 270N. The technical computing worker 270N when it completes processing may return a result back to the automatic task distribution mechanism 260 or the technical computing client 250. This configuration provides for great flexibility in determining how to best distribute technical computing tasks for processing based on many factors such as the types and availability of computing devices, network topology, and the nature and complexity of the technical computing problem being solved.

Many alterations and modifications may be made by those having ordinary skill in the art without departing from the spirit and scope of the invention. Therefore, it must be expressly understood that the illustrated embodiments have been shown only for the purposes of example and should not be taken as limiting the invention, which is defined by the following claims. These claims are to be read as including what they set forth literally and also those equivalent elements which are insubstantially different, even though not identical in other respects to what is shown and described in the above illustrations.

What is claimed is:

1. A method comprising:
receiving a job from a technical computing client implemented on a first computing device,
the receiving the job being performed by a second computing device, and
the job including information identifying:
a first task associated with a first portion of a simulation of a chemical reaction, and
a second task associated with a second portion of the simulation of the chemical reaction;
determining a first technical computing worker, of a plurality of technical computing workers, for performing the first task based on one or more stochastic solvers and a second technical computing worker, of the plurality of technical computing workers, for performing the second task based on the one or more stochastic solvers,
the determining the first technical computing worker and the second technical computing worker being performed by the second computing device;
submitting the first task to the first technical computing worker and the second task to the second technical computing worker,
the submitting being performed by the second computing device,
the first technical computing worker being associated with a first technical computing environment for executing the first task to simulate the first portion of the simulation of the chemical reaction, and
the second technical computing worker being associated with a second technical computing environment for executing the second task to simulate the second portion of the simulation of the chemical reaction;
obtaining a result of executing the first task from the first technical computing worker and a result of executing the second task from the second technical computing worker,
the obtaining being performed by the second computing device; and
providing the result of executing the first task and the result of executing the second task to the first computing device,
the providing being performed by the second computing device.

2. The method of claim 1, further comprising:
providing a model of the chemical reaction to be simulated.

3. The method of claim 1, further comprising:
determining that the job does not specify a particular technical computing worker for performing the first task;
determining that the first technical computing worker is available to perform the first task; and
determining the first technical computing worker for performing the first task based on the first technical computing worker being available to perform the first task.

4. The method of claim 1, where providing the result of executing the first task and the result of executing the second task includes:
determining whether the result of executing the first task has been obtained from the first technical computing worker; and
holding the result of executing the second task until the result of executing the first task has been obtained from the first technical computing worker.

5. The method of claim 1, where one or more properties associated with the job include information identifying a minimum quantity of technical computing workers for performing the job,
the method further comprising:
determining that a quantity of technical computing workers, of the plurality of technical computing workers, that are available for performing the job is greater than or equal to the minimum quantity of technical computing workers; and
starting a processing of the job based on determining that the quantity of technical computing workers that are available for performing the job is greater than or equal to the minimum quantity of technical computing workers.

6. The method of claim 1, where the job includes a plurality of tasks,
the plurality of tasks including the first task and the second task,
where one or more properties associated with the job include information identifying a maximum quantity of technical computing workers for performing the job, and
where the method further comprises:
preventing the plurality of tasks from being distributed to a quantity of technical computing workers, of the plurality of technical computing workers, that exceeds the maximum quantity of technical computing workers.

7. The method of claim 1, further comprising:
determining a version of simulation software that is installed on a computing device associated with the first technical computing worker; and
where determining the first technical computing worker and the second technical computing worker includes:
determining the first technical worker, for performing the first task, based on the version of simulation software that is installed on the computing device associated with the first technical computing worker.

8. A non-transitory computer-readable medium storing instructions, the instructions comprising:
one or more instructions that, when executed by one or more processors of a first computing device, cause the one or more processors to:
receive a job from a technical computing client implemented on a second computing device,
the job including information identifying:
a first task associated with a first portion of a simulation of a chemical reaction, and
a second task associated with a second portion of the simulation of the chemical reaction;
determine a first technical computing worker, of a plurality of technical computing workers, for performing the first task based on one or more stochastic solvers and a second technical computing worker, of the plurality of technical computing workers, for performing the second task based on the one or more stochastic solvers;
submit the first task to the first technical computing worker and the second task the second technical computing worker,
the first technical computing worker being associated with a first technical computing environment for executing the first task to simulate the first portion of the simulation of the chemical reaction, and
the second technical computing worker being associated with a second technical computing environment for executing the second task to simulate the second portion of the simulation of the chemical reaction;

obtain a result of executing the first task from the first technical computing worker and a result of executing the second task from the second technical computing worker; and provide the result of executing the first task and the result of executing the second task to the second computing device.

9. The non-transitory computer-readable medium of claim 8, where the instructions further comprise one or more instructions to determine one or more respective properties associated with each of the plurality of technical computing workers, and where the one or more instructions to determine the one or more respective properties associated with each of the plurality of technical computing workers include:

one or more instructions that, when executed by the one or more processors, cause the one or more processors to:

determine that the second technical computing worker is associated with a computing device that has a higher speed configuration relative to a computing device associated with the first technical computing worker; and where the one or more instructions to submit the first task to the first technical computing worker and the second task to the second technical computing worker include:

one or more instructions that, when executed by the one or more processors, cause the one or more processors to:

submit, to the second technical computing worker, the second task based on:

the computing device associated with the second technical computing device having the higher speed configuration relative to the computing device associated with the first technical computing worker, and a time required to perform the second task being greater than a time required to perform the first task.

10. The non-transitory computer-readable medium of claim 8, where the instructions further comprise one or more instructions to determine the first technical computing worker and the second technical computing worker based on a network topology associated with the first computing device, the second computing device, and computing devices associated with the plurality of technical computing workers.

11. The non-transitory computer-readable medium of claim 8, where the instructions further comprise:

one or more instructions that, when executed by the one or more processors, cause the one or more processors to:

determine that the job does not specify a particular technical computing worker for performing the first task;

determine that the first technical computing worker is available to perform the first task; and determine the first technical computing worker for performing the first task based on the first technical computing worker being available to perform the first task.

12. The non-transitory computer-readable medium of claim 8, where the job includes a plurality of tasks, where the plurality of tasks includes the first task and the second task, and where the one or more instructions to provide the result of executing the first task and the result of executing the second task include:

one or more instructions that, when executed by the one or more processors, cause the one or more processors to:

determine whether a result of an execution of each task, of the plurality of tasks, has been obtained; and provide the result of executing the first task and the result of executing the second task when the result of the execution of each task has been obtained.

13. The non-transitory computer-readable medium of claim 8, where the instructions further comprise:

one or more instructions that, when executed by the one or more processors, cause the one or more processors to:

determine one or more properties associated with the job, where the one or more properties associated with the job include information identifying a minimum quantity of technical computing workers for performing the job, determine, based on the one or more properties, that a quantity of technical computing workers, of the plurality of technical computing workers, that are available for performing the job is greater than or equal to the minimum quantity of technical computing workers; and initiate a processing of the job based on the quantity of technical computing workers that are available for performing the job being greater than or equal to the minimum quantity of technical computing workers.

14. The non-transitory computer-readable medium of claim 8, where the job includes a plurality of tasks, where the plurality of tasks includes the first task and the second task, where one or more properties associated with the job include information identifying a maximum quantity of technical computing workers for performing the job, and where the instructions further comprise:

one or more instructions that, when executed by the one or more processors, cause the one or more processors to:

prevent the plurality of tasks from being distributed to a quantity of technical computing workers, of the plurality of technical computing workers, that exceeds the maximum quantity of technical computing workers.

15. The non-transitory computer-readable medium of claim 8, where the instructions further include:

one or more instructions that, when executed by the one or more processors, cause the one or more processors to:

determine a version of simulation software that is installed on a computing device associated with the first technical computing worker;

determine the first technical computing worker, for performing the first task, based on the version of simulation software that is installed on the computing device associated with the first technical computing worker.

16. A system comprising:

one or more processors to:

receive, from a technical computing client implemented on a computing device, a job associated with a simulation of a chemical reaction, the job being associated with one or more tasks, a first task of the one or more tasks being associated with a first portion of the simulation of the chemical reaction, and a second task of the one or more tasks being associated with a second portion of the simulation of the chemical reaction;

determine a first technical computing worker, of a plurality of technical computing workers, for performing the first task based on one or more stochastic solvers and a second technical computing worker, of the plurality of technical computing workers, for performing the second task based on the one or more stochastic solvers;

provide the first task to the first technical computing worker and the second task to the second technical computing worker;

obtain a first result associated with executing the first task, from the first technical computing worker, and a second result associated with executing the second task from the second technical computing worker; and provide the first result and the second result to the computing device.

17. The system of claim 16, where the one or more processors are further to:
   determine that the job does not specify a particular technical computing worker for performing the first task;
   determine that the first technical computing worker is available to perform the first task; and
   where, when determining the first technical computing worker for performing the first task and the second technical computing worker for performing the second task, the one or more processors are to:
      determine the first technical computing worker for performing the first task based on the first technical computing worker being available to perform the first task.

18. The system of claim 16, where the job includes a plurality of tasks,
   where the plurality of tasks includes the first task and the second task, and
   where, when providing the first result and the second result, the one or more processors are to:
      determine whether a result of an execution of each task, of the plurality of tasks, has been obtained; and
      provide the first result and the second result when the result of the execution of each task has been obtained.

19. The system of claim 16, where one or more properties associated with the job include information identifying a minimum quantity of technical computing workers for performing the job, and
   where the one or more processors are further to:
      determine that a quantity of technical computing workers, of the plurality of technical computing workers, that are available for performing the job is greater than or equal to the minimum quantity of technical computing workers; and
      initiate a processing of the job based on the quantity of technical computing workers that are available for performing the job being greater than or equal to the minimum quantity of technical computing workers.

20. The system of claim 16, where the job includes a plurality of tasks,
   where the plurality of tasks includes the first task and the second task,
   where one or more properties associated with the job include information identifying a maximum quantity of technical computing workers for performing the job, and
   where the one or more processors are further to:
      prevent the plurality of tasks from being distributed to a quantity of technical computing workers, of the plurality of technical computing workers, that exceeds the maximum quantity of technical computing workers.

21. The system of claim 16, where the one or more processors are to:
   determine a version of simulation software that is installed on a computing device associated with the first technical computing worker; and
   determine the first technical computing worker, for performing the first task, based on the version of simulation software that is installed on the computing device associated with the first technical computer worker.

* * * * *